United States Patent
Gamble et al.

(10) Patent No.: US 9,879,255 B2
(45) Date of Patent: Jan. 30, 2018

(54) MODULATION OF RNA ACTIVITY AND VASCULAR PERMEABILITY

(71) Applicants: Centenary Institute of Cancer Medicine and Cell Biology, Camperdown (AU); Mirrx Therapeutics A/S, Vejle (DK); The University of Sydney, Sydney (AU)

(72) Inventors: Jennifer Gamble, Double Bay (AU); Mathew Vadas, Double Bay (AU); Thorleif Moller, Vejle (DK)

(73) Assignee: University of Newcastle Upon Tyne, Newcastle Upon Tyne (GB)

(*) Notice: Subject to any disclaimer, the term of this patent is extended or adjusted under 35 U.S.C. 154(b) by 0 days.

(21) Appl. No.: 14/433,150

(22) PCT Filed: Oct. 2, 2013

(86) PCT No.: PCT/AU2013/001129
§ 371 (c)(1),
(2) Date: Apr. 2, 2015

(87) PCT Pub. No.: WO2014/053014
PCT Pub. Date: Apr. 10, 2014

(65) Prior Publication Data
US 2016/0040160 A1    Feb. 11, 2016

(30) Foreign Application Priority Data

Oct. 2, 2012 (AU) ................ 2012904297
Oct. 5, 2012 (AU) ................ 2012904365

(51) Int. Cl.
*A61K 48/00* (2006.01)
*C07H 21/02* (2006.01)
*C07H 21/04* (2006.01)
*C12N 15/113* (2010.01)

(52) U.S. Cl.
CPC ........ *C12N 15/113* (2013.01); *C12N 2310/11* (2013.01); *C12N 2310/113* (2013.01); *C12N 2310/321* (2013.01); *C12N 2310/323* (2013.01); *C12N 2310/3231* (2013.01)

(58) Field of Classification Search
CPC .... C12N 2310/11; C12N 15/113; A61K 48/00
See application file for complete search history.

(56) References Cited

U.S. PATENT DOCUMENTS

| 8,076,472 | B2* | 12/2011 | McSwiggen | A61K 47/48053 |
| | | | | 536/23.1 |
| 8,691,965 | B2 | 4/2014 | Møller | |
| 8,951,984 | B2 | 2/2015 | Møller | |
| 9,290,767 | B2 | 3/2016 | Moeller et al. | |
| 2010/0021914 | A1 | 1/2010 | Møller | |
| 2013/0079505 | A1 | 3/2013 | Moeller et al. | |
| 2015/0344892 | A1 | 12/2015 | Moeller et al. | |
| 2016/0145620 | A1 | 5/2016 | Moeller | |

FOREIGN PATENT DOCUMENTS

| AU | 2007323469 A1 | 5/2008 |
| AU | 2008261404 A1 | 12/2008 |
| AU | 2014250708 A1 | 11/2014 |
| AU | 2013324716 A1 | 4/2015 |
| CA | 2681568 A1 | 5/2008 |
| CA | 2690643 A1 | 12/2008 |
| CA | 2886116 A1 | 4/2014 |
| CN | 104955950 A | 9/2015 |
| EP | 2097527 A2 | 9/2009 |
| EP | 2550360 A1 | 1/2013 |
| EP | 2643341 A1 | 10/2013 |
| EP | 2714904 A2 | 4/2014 |
| EP | 2908822 A1 | 8/2015 |
| IN | 3370/DELNP/2015 A | 10/2016 |
| JP | 2015146814 A | 8/2015 |
| JP | 2016513950 A | 5/2016 |
| WO | WO-2008/061537 A2 | 5/2008 |
| WO | WO-2010/139026 A1 | 12/2010 |
| WO | WO-2014/053014 A1 | 4/2014 |

OTHER PUBLICATIONS

"International Application Serial No. PCT/AU2013/001129, International Preliminary Report on Patentability dated Apr. 7, 2015", 6 pgs.
"International Application Serial No. PCT/AU2013/001129, International Search Report mailed Nov. 20, 2013", 3 pgs.
"International Application Serial No. PCT/AU2013/001129, Written Opinion mailed Nov. 20, 2013", 5 pgs.
Young, J. A., et al., "Regulation of vascular leak and recovery from ischemic injury by general and VE-cadherin-restricted miRNA antagonists of miR-27", *Blood*, 122(16), (2013), 2911-2919.

* cited by examiner

*Primary Examiner* — Amy Bowman
(74) *Attorney, Agent, or Firm* — Schwegman Lundberg & Woessner, P.A.

(57) ABSTRACT

The present invention provides oligonucleotides that inhibit the binding of miR-27a to VE-cadherin mRNA, particularly in the form of blockmirs. The invention also provides compositions comprising such oligonucleotides and methods of use of such oligonucleotides to modulate the activity of VE-cadherin, inhibit or reduce vascular permeability, treat or prevent a vascular permeability-associated disease or condition, inhibit tumor growth, treat ischaemic injury, enhance recovery from ischaemic injury, treat surgical wounds and/or promotes post-operative recovery, and promote or induce angiogenesis.

16 Claims, 7 Drawing Sheets

SEQUENCE LISTING

<160> NUMBER OF SEQ ID NOS: 11

<210> SEQ ID NO 1
<211> LENGTH: 6
<212> TYPE: RNA
<213> ORGANISM: Homo sapiens

<400> SEQUENCE: 1 cuguga                                                                      6

<210> SEQ ID NO 2
<211> LENGTH: 45
<212> TYPE: RNA
<213> ORGANISM: Homo sapiens

<400> SEQUENCE: 2
gcuuauuaaa cuuugaagca acugugaauu cauucuggag gggca            45

<210> SEQ ID NO 3
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 3
tucacagutg cuuca                                                           15

<210> SEQ ID NO 4
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 4
tucacagutg cttca                                                           15

<210> SEQ ID NO 5
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: LNA
<220> FEATURE:
<221> NAME/KEY: modified_base
<222> LOCATION: (2)..(2)
<223> OTHER INFORMATION: 2' O-methyl uridine
<220> FEATURE:
<221> NAME/KEY: modified_base
<222> LOCATION: (3)..(3)
<223> OTHER INFORMATION: LNA
<220> FEATURE:
<221> NAME/KEY: modified_base
<222> LOCATION: (4)..(4)
<223> OTHER INFORMATION: 2' O-methyl adenosine
<220> FEATURE:
<221> NAME/KEY: modified_base
<222> LOCATION: (5)..(5)
<223> OTHER INFORMATION: LNA
<220> FEATURE:
<221> NAME/KEY: modified_base
<222> LOCATION: (6)..(6)
<223> OTHER INFORMATION: 2' O-methyl adenosine
<220> FEATURE:
<221> NAME/KEY: modified_base

```
<222> LOCATION: (7)..(7)
<223> OTHER INFORMATION: LNA
<220> FEATURE:
<221> NAME/KEY: modified_base
<222> LOCATION: (8)..(8)
<223> OTHER INFORMATION: 2' O-methyl uridine
<220> FEATURE:
<221> NAME/KEY: modified_base
<222> LOCATION: (9)..(9)
<223> OTHER INFORMATION: LNA
<220> FEATURE:
<221> NAME/KEY: modified_base
<222> LOCATION: (10)..(10)
<223> OTHER INFORMATION: 2' O-methyl guanosine
<220> FEATURE:
<221> NAME/KEY: modified_base
<222> LOCATION: (11)..(11)
<223> OTHER INFORMATION: 2' O-methyl cytidine
<220> FEATURE:
<221> NAME/KEY: modified_base
<222> LOCATION: (12)..(12)
<223> OTHER INFORMATION: LNA
<220> FEATURE:
<221> NAME/KEY: modified_base
<222> LOCATION: (13)..(13)
<223> OTHER INFORMATION: 2' O-methyl uridine
<220> FEATURE:
<221> NAME/KEY: modified_base
<222> LOCATION: (14)..(15)
<223> OTHER INFORMATION: LNA

<400> SEQUENCE: 5
tucacagutg cuuca                                              15

<210> SEQ ID NO 6
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: LNA
<220> FEATURE:
<221> NAME/KEY: modified_base
<222> LOCATION: (2)..(2)
<223> OTHER INFORMATION: 2' O-methyl uridine
<220> FEATURE:
<221> NAME/KEY: modified_base
<222> LOCATION: (3)..(3)
<223> OTHER INFORMATION: 2' O-methyl cytidine
<220> FEATURE:
<221> NAME/KEY: modified_base
<222> LOCATION: (4)..(4)
<223> OTHER INFORMATION: 2' O-methyl adenosine
<220> FEATURE:
<221> NAME/KEY: modified_base
<222> LOCATION: (5)..(5)
<223> OTHER INFORMATION: 2' O-methyl cytidine
<220> FEATURE:
<221> NAME/KEY: modified_base
<222> LOCATION: (6)..(6)
<223> OTHER INFORMATION: 2' O-methyl adenosine
<220> FEATURE:
<221> NAME/KEY: modified_base
<222> LOCATION: (7)..(7)
<223> OTHER INFORMATION: 2' O-methyl guanosine
<220> FEATURE:
<221> NAME/KEY: modified_base
<222> LOCATION: (8)..(8)
<223> OTHER INFORMATION: 2' O-methyl uridine
<220> FEATURE:
<221> NAME/KEY: modified_base
<222> LOCATION: (9)..(15)
<223> OTHER INFORMATION: LNA
```

<400> SEQUENCE: 6
tucacagutg cttca                                                          15

<210> SEQ ID NO 7
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: LNA
<220> FEATURE:
<221> NAME/KEY: modified_base
<222> LOCATION: (2)..(2)
<223> OTHER INFORMATION: 2' O-methyl uridine
<220> FEATURE:
<221> NAME/KEY: modified_base
<222> LOCATION: (3)..(3)
<223> OTHER INFORMATION: 2' O-methyl cytidine
<220> FEATURE:
<221> NAME/KEY: modified_base
<222> LOCATION: (4)..(4)
<223> OTHER INFORMATION: 2' O-methyl adenosine
<220> FEATURE:
<221> NAME/KEY: modified_base
<222> LOCATION: (5)..(5)
<223> OTHER INFORMATION: UNA
<220> FEATURE:
<221> NAME/KEY: modified_base
<222> LOCATION: (6)..(6)
<223> OTHER INFORMATION: 2' O-methyl adenosine
<220> FEATURE:
<221> NAME/KEY: modified_base
<222> LOCATION: (7)..(7)
<223> OTHER INFORMATION: 2' O-methyl guanosine
<220> FEATURE:
<221> NAME/KEY: modified_base
<222> LOCATION: (8)..(8)
<223> OTHER INFORMATION: 2' O-methyl uridine
<220> FEATURE:
<221> NAME/KEY: modified_base
<222> LOCATION: (9)..(15)
<223> OTHER INFORMATION: LNA

<400> SEQUENCE: 7
tucacagutg cttca                                                          15

<210> SEQ ID NO 8
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: LNA
<220> FEATURE:
<221> NAME/KEY: modified_base
<222> LOCATION: (2)..(2)
<223> OTHER INFORMATION: 2' O-methyl uridine
<220> FEATURE:
<221> NAME/KEY: modified_base
<222> LOCATION: (3)..(3)
<223> OTHER INFORMATION: LNA
<220> FEATURE:
<221> NAME/KEY: modified_base
<222> LOCATION: (4)..(4)
<223> OTHER INFORMATION: 2' O-methyl adenosine
<220> FEATURE:
<221> NAME/KEY: modified_base
<222> LOCATION: (5)..(5)
<223> OTHER INFORMATION: 2' O-methyl guanosine

```
<220> FEATURE:
<221> NAME/KEY: modified_base
<222> LOCATION: (6)..(6)
<223> OTHER INFORMATION: LNA
<220> FEATURE:
<221> NAME/KEY: modified_base
<222> LOCATION: (7)..(7)
<223> OTHER INFORMATION: 2' O-methyl cytidine
<220> FEATURE:
<221> NAME/KEY: modified_base
<222> LOCATION: (8)..(8)
<223> OTHER INFORMATION: 2' O-methyl adenosine
<220> FEATURE:
<221> NAME/KEY: modified_base
<222> LOCATION: (9)..(9)
<223> OTHER INFORMATION: LNA
<220> FEATURE:
<221> NAME/KEY: modified_base
<222> LOCATION: (10)..(10)
<223> OTHER INFORMATION: 2' O-methyl uridine
<220> FEATURE:
<221> NAME/KEY: modified_base
<222> LOCATION: (11)..(11)
<223> OTHER INFORMATION: 2' O-methyl guanosine
<220> FEATURE:
<221> NAME/KEY: modified_base
<222> LOCATION: (12)..(12)
<223> OTHER INFORMATION: LNA
<220> FEATURE:
<221> NAME/KEY: modified_base
<222> LOCATION: (13)..(13)
<223> OTHER INFORMATION: 2' O-methyl guanosine
<220> FEATURE:
<221> NAME/KEY: modified_base
<222> LOCATION: (14)..(15)
<223> OTHER INFORMATION: LNA

<400> SEQUENCE: 8
cutagccacu gtgaa                                                          15

<210> SEQ ID NO 9
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: LNA
<220> FEATURE:
<221> NAME/KEY: modified_base
<222> LOCATION: (2)..(2)
<223> OTHER INFORMATION: 2' O-methyl cytidine
<220> FEATURE:
<221> NAME/KEY: modified_base
<222> LOCATION: (3)..(3)
<223> OTHER INFORMATION: LNA
<220> FEATURE:
<221> NAME/KEY: modified_base
<222> LOCATION: (4)..(4)
<223> OTHER INFORMATION: 2' O-methyl adenosine
<220> FEATURE:
<221> NAME/KEY: modified_base
<222> LOCATION: (5)..(5)
<223> OTHER INFORMATION: LNA
<220> FEATURE:
<221> NAME/KEY: modified_base
<222> LOCATION: (6)..(6)
<223> OTHER INFORMATION: 2' O-methyl adenosine
<220> FEATURE:
<221> NAME/KEY: modified_base
<222> LOCATION: (7)..(7)
<223> OTHER INFORMATION: LNA
<220> FEATURE:
<221> NAME/KEY: modified_base
<222> LOCATION: (8)..(8)
```

```
<223> OTHER INFORMATION: 2' O-methyl adenosine
<220> FEATURE:
<221> NAME/KEY: modified_base
<222> LOCATION: (9)..(9)
<223> OTHER INFORMATION: LNA
<220> FEATURE:
<221> NAME/KEY: modified_base
<222> LOCATION: (10)..(11)
<223> OTHER INFORMATION: 2' O-methyl guanosine
<220> FEATURE:
<221> NAME/KEY: modified_base
<222> LOCATION: (12)..(12)
<223> OTHER INFORMATION: LNA
<220> FEATURE:
<221> NAME/KEY: modified_base
<222> LOCATION: (13)..(13)
<223> OTHER INFORMATION: 2' O-methyl uridine
<220> FEATURE:
<221> NAME/KEY: modified_base
<222> LOCATION: (14)..(15)
<223> OTHER INFORMATION: LNA

<400> SEQUENCE: 9
tccagagatg gtuga                                                          15

<210> SEQ ID NO 10
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: LNA
<220> FEATURE:
<221> NAME/KEY: modified_base
<222> LOCATION: (2)..(2)
<223> OTHER INFORMATION: 2' O-methyl uridine
<220> FEATURE:
<221> NAME/KEY: modified_base
<222> LOCATION: (3)..(3)
<223> OTHER INFORMATION: 2' O-methyl cytidine
<220> FEATURE:
<221> NAME/KEY: modified_base
<222> LOCATION: (4)..(4)
<223> OTHER INFORMATION: 2' O-methyl adenosine
<220> FEATURE:
<221> NAME/KEY: modified_base
<222> LOCATION: (5)..(5)
<223> OTHER INFORMATION: 2' O-methyl cytidine
<220> FEATURE:
<221> NAME/KEY: modified_base
<222> LOCATION: (6)..(6)
<223> OTHER INFORMATION: 2' O-methyl adenosine
<220> FEATURE:
<221> NAME/KEY: modified_base
<222> LOCATION: (7)..(7)
<223> OTHER INFORMATION: 2' O-methyl guanosine
<220> FEATURE:
<221> NAME/KEY: modified_base
<222> LOCATION: (8)..(8)
<223> OTHER INFORMATION: 2' O-methyl uridine
<220> FEATURE:
<221> NAME/KEY: modified_base
<222> LOCATION: (9)..(15)
<223> OTHER INFORMATION: LNA

<400> SEQUENCE: 10
tucacaguaa atttc                                                          15

<210> SEQ ID NO 11
<211> LENGTH: 21
<212> TYPE: RNA
<213> ORGANISM: Homo sapiens
```

```
<400> SEQUENCE: 11
uucacagugg cuaaguuccg c                                              21
```

MODULATION OF RNA ACTIVITY AND VASCULAR PERMEABILITY

FIELD OF THE INVENTION

The present invention relates generally to oligonucleotides that can be used to affect the activity of a target RNA, specifically CDH5 or VE-cadherin mRNA. More particularly, the oligonucleotides of the invention inhibit the binding of miR-27a to VE-cadherin mRNA. The present invention also relates to the use of such oligonucleotides to inhibit vascular permeability or vascular leak and treat diseases and conditions associated therewith.

BACKGROUND OF THE INVENTION

Antisense Oligonucleotides

The first generation of antisense oligonucleotides were intended to affect the activity of target mRNAs. One reason for interest in such oligonucleotides is the potential for exquisite and predictable specificity that can be achieved because of specific base pairing. It is in theory very simple to design an oligonucleotide that is highly specific for a given nucleic acid, such as an mRNA. However simple base pairing is not enough to achieve regulation of a given target mRNA. That is, an oligonucleotide complementary to a given target mRNA does not necessarily affect the activity of the target mRNA. If the oligonucleotide targets the open reading frame of an mRNA, it may, for example, be that the translational apparatus simply displaces the oligonucleotide during translation. Therefore, means were developed that would improve the regulatory activity of the oligonucleotide, including oligonucleotides that can activate RNase H cleavage of the target mRNA. However one disadvantage of such oligonucleotides is that they may mediate cleavage of RNAs other than the intended target mRNA giving rise to off-target effects. Notwithstanding, several oligonucleotides acting through RNase H cleavage are in clinical trial for the treatment of various diseases.

More recently research has shown that eukaryotic cells, including mammalian cells, comprise a complex gene regulatory system (RNAi machinery) that uses RNA as specificity determinants. This system can be triggered by small interfering RNA (siRNA) that may be introduced into a cell of interest to regulate the activity of a target mRNA. Currently, considerable effort goes into using siRNA as novel therapeutics to trigger RNAi machinery for specific regulation of target RNAs, in particular target mRNAs. However siRNAs are proving less specific than initially thought and result in significant off-target effects. It is now believed that these off-targets stem from the siRNAs, or rather the guide strand of the siRNAs, acting as microRNAs.

MicroRNAs

MicroRNAs (miRNAs) are a class of endogenous RNA molecules that, like siRNA, function via the RNAi machinery. miRNAs are small, single stranded, non-coding RNAs which regulate both mRNA degradation and translation, at least partially through their ability to bind to the 3'UTR of target genes through base pairing with the 5'-end of the miRNA, via the so called seed sequence or seed region of the miRNA.

Currently, more than 500 human miRNAs have been discovered and it is believed that more than one third of all human genes are regulated by miRNAs. Therefore, miRNAs themselves may be used to regulate the activity of target RNAs, opening the opportunity to develop miRNAs as therapeutics. However, miRNAs generally act at more than one target RNA; they are promiscuous. Thus, introduction of a miRNA into a cell or regulating the level of a miRNA in a cell will affect the activity of more than one target mRNA and consequently may give rise to unexpected and undesired effects.

miRNAs can be inhibited using complementary oligonucleotides, termed antimirs and antagomirs. However since each miRNA is itself promiscuous, any given antimir or antagomir will similarly affect the activity of more than one target mRNA.

miRNA and Angiogenesis

The tight control of vascular permeability is one of the chief functions of the endothelial lining of blood vessels. A loss of this barrier function of endothelium underlies many general and organ specific disease processes including leakiness of tumor vessels, various respiratory distress syndromes, complications of chemotherapy as well as acute anaphylactoid reactions. Controls of permeability generally fall into two classes: one the stimuli, like thrombin, histamine, vascular endothelial growth factor (VEGF), that induce leakiness. The other, a class of molecules like angiopoetin-1 that exert a tonic effect on sustaining the status quo. Ultimately these two influences converge on the cell-cell junctional molecules such as VE Cadherin and PECAM that regulate junctional structure.

Given the relatively clear phenotypes induced by these stimuli it is surprising how self-limited the leakiness is under circumstances of repair or physiological angiogenesis. The inventors reasoned that there may exist yet undiscovered mechanisms that will operate to force a quick restoration to normality of vessels, for example in the process of angiogenesis, or that operate during physiological angiogenesis to limit the leakiness of newly forming vessels. This would be in stark contrast to tumour angiogenic vessels that are characterized by excessive leakiness, where these control mechanisms may be by-passed.

In the vasculature, miRNAs have been linked to regulation of development, and to diseases such as tumour growth and cardiovascular disease. For example, the endothelial cell-restricted miRNA, miR-126, is highly expressed during vascular development and tumour angiogenesis, while in contrast miR-101 is downregulated in tumour vessels, acting through histone-methyltransferase to promote angiogenesis. In endothelial cells miR-296 is VEGF responsive and blockade of this miRNA inhibits tumour-associated angiogenesis. miR-132 is induced in tumour angiogenic vessels, targeting p120RasGAP which acts downstream of integrins to increase cell proliferation and vascular growth. miR-92a targets integrin signalling and its inhibition improves blood flow recovery following ischemic insult.

SUMMARY OF THE INVENTION

The present invention relates to oligonucleotides for modulating the activity of a target RNA. The oligonucleotides of the invention may be capable or incapable of recruiting RNase H and/or the RNAi machinery when bound to a target site.

Disclosed herein are oligonucleotides comprising sequences complementary to, and capable of binding to, the sequence shown in SEQ ID NO:1. Typically the oligonucleotides comprise sequences complementary to, and capable of binding to, contiguous sequences of the 3' untranslated region (3'UTR) of the VE-cadherin (CDH5) mRNA molecule, comprising the sequence shown in SEQ ID NO:1.

In a first aspect the present invention provides an oligonucleotide comprising a contiguous sequence complementary to at least 8 contiguous bases of an RNA sequence comprising SEQ ID NO: 2, or SEQ ID NO: 2 comprising 1, 2 or 3 substitutions, wherein the oligonucleotide inhibits the binding of miR-27a, a variant thereof or a miRNA comprising a seed region comprising the sequence UCACAG, to said RNA.

Typically the miR-27a miRNA is hsa-miR-27a comprising the nucleotide sequence set forth in SEQ ID NO:11.

In an embodiment, the oligonucleotide comprises a contiguous sequence complementary to a sequence of at least or about 7 bases, at least or about 8 bases, at least or about 9 bases, at least or about 10 bases, at least or about 11 bases, at least or about 12 bases, at least or about 13 bases, at least or about 14 bases, at least or about 15 bases, at least or about 16 bases, at least or about 17 bases, at least or about 18 bases, at least or about 19 bases, at least or about 20 bases, at least or about 22 bases, at least or about 25 bases, at least or about 30 bases, or at least or about 35 bases of SEQ ID NO: 2, or SEQ ID NO: 2 comprising 1, 2 or 3 substitutions.

Typically the oligonucleotide binds to positions 22-27 of SEQ ID NO: 2.

In a particular embodiment, base pairing between the oligonucleotide and SEQ ID NO: 2 includes positions 8-28, 8-27, 9-27, 10-27, 11-27, 12-27, 13-27, 14-27, 15-27, 16-27, 17-27, 18-27, 19-27, 20-27, 21-27, 9-28, 10-28, 11-28, 12-28, 13-28, 14-28, 15-28, 16-28, 17-28, 18-28, 19-28, 20-28 or 21-28 of SEQ ID NO: 2.

In a further particular embodiment, the oligonucleotide comprises the sequence set forth in SEQ ID NO: 3 or SEQ ID NO: 4.

In a further particular embodiment, the oligonucleotide comprises one or more modified nucleobases. In exemplary embodiments, the modified nucleobase may be selected from an LNA nucleobase, a UNA nucleobase and a 2' O-methyl nucleobase.

In a further particular embodiment, the oligonucleotide comprises a sequence set forth in SEQ ID NO: 5, SEQ ID NO: 6 or SEQ ID NO: 7.

In a second aspect the present invention provides a composition comprising an oligonucleotide of any one of claims 1 to 8.

In an embodiment, the composition is a pharmaceutical composition comprising one or more pharmaceutically acceptable carriers, excipients or diluents.

In a third aspect the present invention provides method for modulating the activity of VE-cadherin in a cell, the method comprising contacting the cell with an effective amount of an oligonucleotide of the first aspect to thereby modulate the activity of the VE-cadherin.

In particular embodiments, modulating the activity of VE-cadherin inhibits or reduces vascular permeability, treats or prevents a vascular permeability-associated disease or condition, inhibits tumour growth, treats ischaemic injury, enhances recovery from ischaemic injury, treats surgical wounds and/or promotes post-operative recovery, or promotes or induces angiogenesis.

In a fourth aspect the present invention provides a method for inhibiting or reducing vascular permeability in a vascular vessel, the method comprising contacting the vessel with an effective amount of an oligonucleotide of the first aspect or a composition of the second aspect.

In a fifth aspect the present invention provides a method for inhibiting or reducing vascular permeability in a subject in need of such treatment, the method comprising administering to the subject an effective amount of an oligonucleotide of the first aspect or a composition of the second aspect.

In a sixth aspect the present invention provides a method for treating or preventing a vascular permeability-associated disease or condition in a subject, the method comprising administering to the subject an effective amount of an oligonucleotide of the first aspect or a composition of the second aspect.

The vascular permeability-associated disease or condition may be selected from oedema, cardiovascular disease, myocardial infarction, peripheral vascular disease, ischaemia, stroke, cancer, atherosclerosis, psoriasis, diabetes, autoimmune diseases such as rheumatoid arthritis, thrombocytopenia, altitude sickness, barotrauma, iatrogenic disorders, bacterial infections, viral infections, and ocular conditions associated with vascular leak such as non-proliferative and proliferative retinopathies (including diabetic retinopathy), macular oedema (including diabetic macular oedema), glaucoma and macular degeneration (including age-related macular degeneration).

In particular embodiments the oedema may be, for example, cardiac oedema, pulmonary oedema, renal oedema, macular oedema, cerebral oedema, malnutritional oedema or lymphoedema. The oedema may result from a surgical procedure, in particular a major surgical procedure, such as cardiac surgery, organ transplantation surgery, knee and hip replacement surgery, dental surgery or limb amputation surgery (for example associated with diabetic complications).

In a seventh aspect the present invention provides a method for treating or preventing oedema in a subject, the method comprising administering to the subject an effective amount of an oligonucleotide of the first aspect or a composition of the second aspect.

In an eighth aspect the present invention provides a method for inhibiting tumour growth in a subject, the method comprising administering to the subject an effective amount of an oligonucleotide of the first aspect or a composition of the second aspect.

In a ninth aspect the present invention provides a method for treating and/or enhancing recovery from ischaemic injury, the method comprising administering to a subject in need of such treatment an effective amount of an oligonucleotide of the first aspect or a composition of the second aspect.

In a tenth aspect the present invention provides a method for promoting or inducing angiogenesis in cells or tissue of a subject, the method comprising administering to the subject, or to cells or tissue derived therefrom, an effective amount of an oligonucleotide of the first aspect or a composition of the second aspect.

The promotion or inducement of angiogenesis may, for example, be for wound healing (including surgical wounds), tissue repair, tissue regeneration or tissue engineering. The angiogenesis may be, for example, post-operative angiogenesis.

In an eleventh aspect the present invention provides a method for treating surgical wounds and for promoting post-operative recovery, the method comprising administering to a subject in need thereof an effective amount of an oligonucleotide of the first aspect or a composition of the second aspect.

In accordance with the tenth and eleventh aspects, the surgical wound may be any wound resulting from surgery or induced in the course of surgery including, for example, those associated with dental surgery, cardiac surgery, organ transplantation surgery, knee and hip replacement surgery and limb amputations (for example associated with diabetic complications).

Also provided is an oligonucleotide of the first aspect for use in the inhibition or reduction in vascular permeability, the treatment or prevention of vascular permeability-associated disease or condition, inhibition of tumour growth, the treatment and/or enhancement of recovery from ischaemic injury, or the promotion or inducement of angiogenesis.

Also provided is the use of an oligonucleotide of the first aspect for the manufacture of a medicament for inhibiting or reducing vascular permeability, treating or preventing a vascular permeability-associated disease or condition, treating or preventing oedema, inhibiting tumour growth, treating and/or enhancing recovery from ischaemic injury, promoting or inducing angiogenesis, and/or treating surgical wounds and promoting post-operative recovery.

Also provided is the use of an oligonucleotide of the first aspect as a research tool for investigating, for example, VE-cadherin activity, vascular permeability and angiogenesis and potential treatments and therapies therefor.

BRIEF DESCRIPTION OF THE DRAWINGS

Embodiments of the invention are described herein, by way of non-limiting example only, with reference to the following figures.

(A) Expression of VE-cadherin in control or miR-27a mimic transfected cells after for 48 h. β-actin was used as a loading control. (B) The normalized expression of mean of five independent HUVEC lines±SEM. *, $p<0.05$ cf control. (C) The level of surface VE-cadherin as assessed by flow cytometry. Solid line, control mimic; dashed line, miR-27a mimic. Result of one experiment shown (similar to three performed). (D) The level of VE-cadherin mRNA expression 24 h post transfection with miR-27a. Results normalized to β-actin are the mean of quadruplicate qRT-PCR reactions±SEM from five independent HUVEC lines. * $p<0.05$ cf control. (E) VE-cadherin expression from HUVEC 24*h* post transfection with control or anti-miR-27a transfected cells. (F) Mean of three independent HUVEC lines±SEM is shown. ***, $p<0.001$ cf control. (G) The level of surface VE-cadherin as, assessed by flow cytometry. Solid line, control LNA; dashed line, LNA-27. Result of one experiment shown (similar to two performed). (H) Luciferase constructs containing the 3'UTR of VE-cadherin containing the putative miR-27a binding site (Wt, black bars) or a mutated miR-27a binding site (Mut, white bars), in HEK293T cells together with control or miR-27a mimic. Results represent the mean of triplicate transfections±SEM from four independent experiments. * $p=0.01$, Wt+miR-27a vs. Mut+miR-27a. ** $p=0.00001$, Wt+control vs. Wt+miR-27a.

Figure 2:
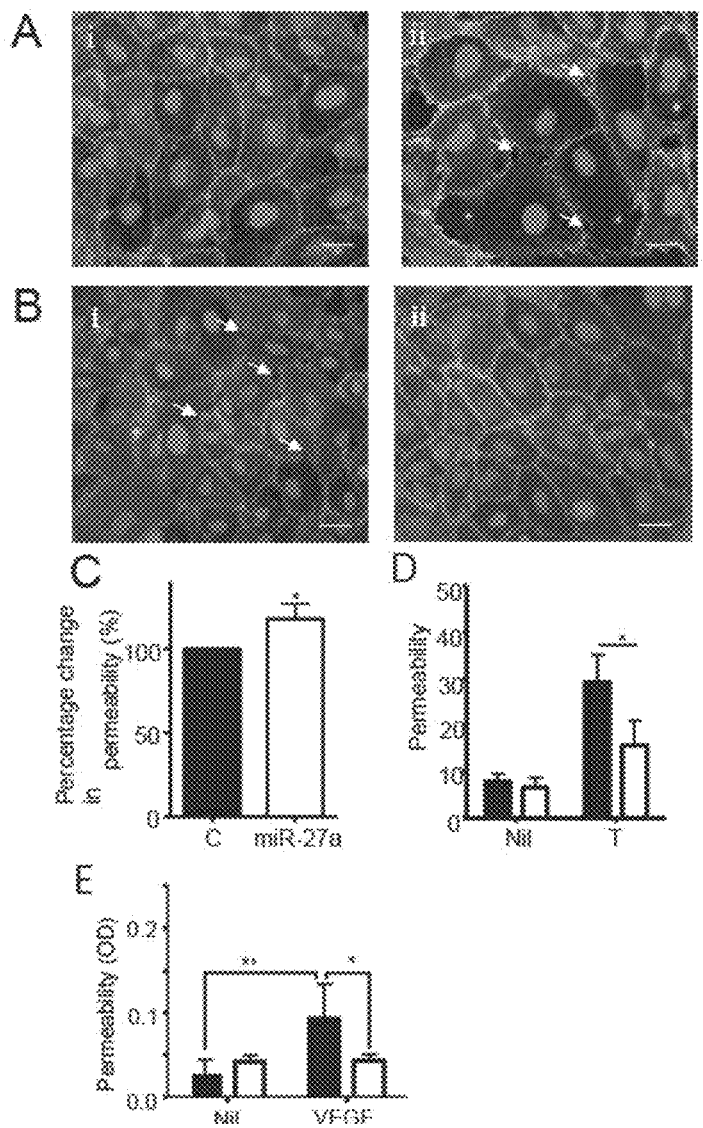

FIG. 2. miR-27a alters VE-cadherin localisation and endothelial cell permeability.

(A), (B) HUVEC were stained for VE-cadherin, 48 hrs after transfection. (A) Control mimic (i) or (ii) miR-27a mimic (B) (i) control LNA, (ii) miR-27 LNA. Scale bar: 100 μm. (C) Permeability measured in control or miR-27a mimic transfected cells after 48 hours. Results shown are the normalized means of five independent HUVEC lines±SEM.*, $p<0.05$ cf control. (D) Permeability measured without (NIL) or after thrombin stimulation (T) in control LNA (black) or miR-27 LNA transfected cells (white). Results are from one experiment representative of 3 performed mean±SEM * $p<0.05$. (E) The Miles assay was performed with 4 μg of control (black) or anti-miR-27a (white bars) injected intradermally into the back of the mice. 24 hours later VEGF or PBS (NIL) as control was given into the same site. * $p<0.01$ ** $p<0.001$, n=9 mice per group.

Figure 3:
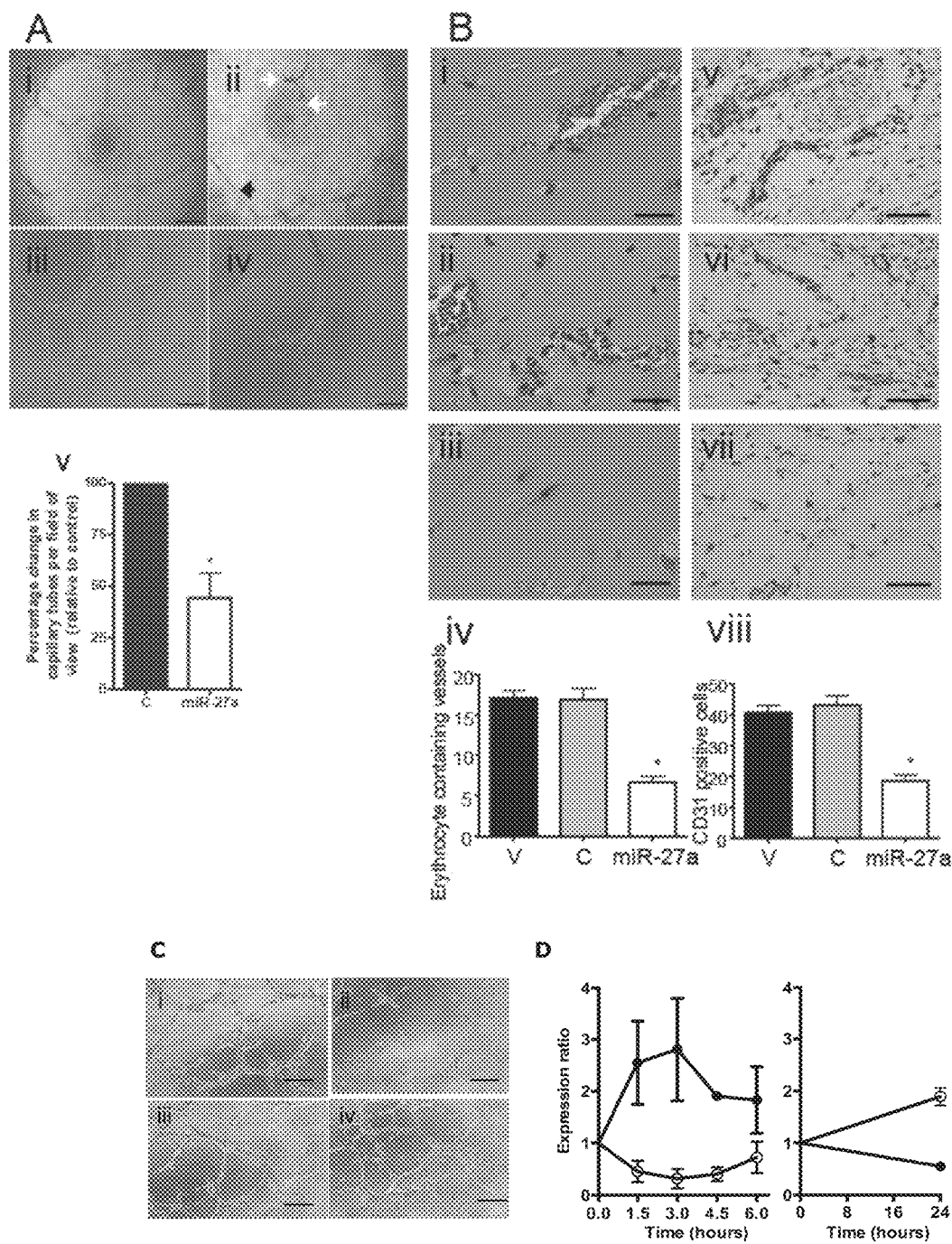

FIG. 3. Overexpression of miRNA-27a reduces in vivo capillary tube formation while miR-27a inhibition reduces in vivo permeability.

(A) HUVEC transfected with a control (i and iii) or miR-27a mimic (ii and iv) and plated onto Matrigel. Retracted tubes: white arrows. Very thin tubes: black arrow. (i) and (ii) Scale bar: 200 μm. (iii), (iv) Scale bar: 400 μm (v) Number of capillary tubes formed per field of view, expressed as a percent relative to the control. * $p<0.05$ cf control. Mean of four independent HUVEC lines±SEM. (B) Mice were implanted subcutaneously with Matrigel plugs containing FGF-2 and vehicle only (i, v), control (ii, vi) or miRNA-27a mimic (iii, vii). Representative histologic sections and hematoxylin and eosin stained cross-sections (i-iii) scale bar: 20 μm. Number of erythrocyte containing vessels quantified (iv). Representative CD31 immunochemistry, (v-vii). Scale bar: 50 μm. Number of CD31 positive cells quantified (viii). Data is expressed as mean±SEM. Statistical analysis of differences was compared by one-way ANOVA with Bonferroni's correction for multiple comparisons. For control (C) n=3 mice and for miRNA-27a and vehicle (V) n=6 mice. (C) Reversal of effect of miR-27a mimics by overexpression of VE-cadherin. Cells were transfected with control mimic (i), miR-27a mimics (ii), VE-cadherin plasmid+control mimics (iii), or VE-cadherin expression plasmid+miR-27a mimics (iv). 24 hours later cells were plated onto Matrigel and viewed over 24 hours. (D) Expression of miR-27a (open circles) and VE-cadherin mRNA (closed circles) over time after wounding monolayers of EC. Data is normalized to levels in the confluent cells. Expression levels were measured by qRT-PCR with results of miR-27a normalized to U48 and VE-cadherin normalized to β-actin. Results are from 2-4 independent HUVEC lines.

Figure 4:
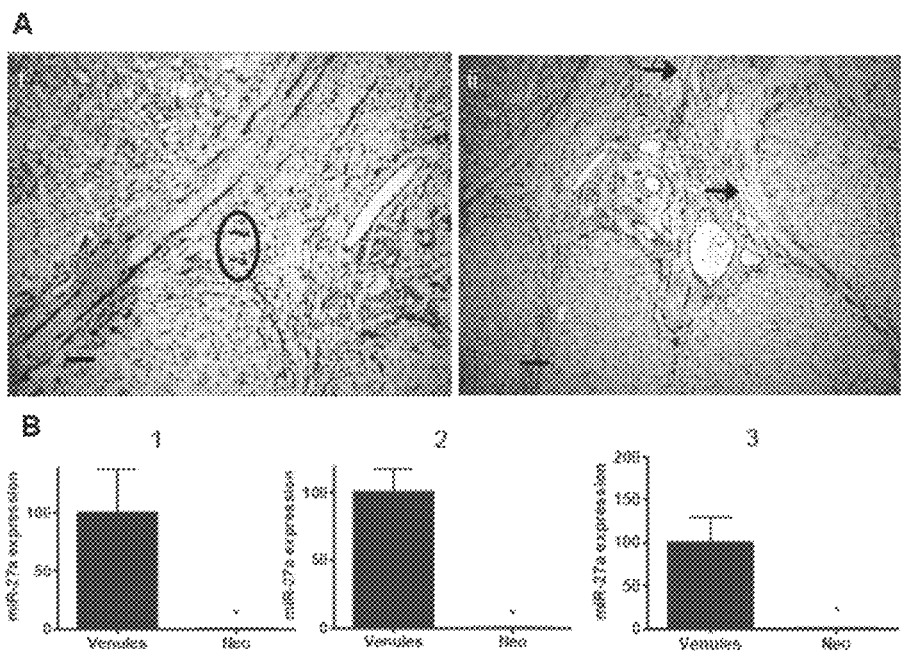

FIG. 4. Regulation of miR-27a in human disease.

Human liver tissue from three patients with cirrhosis was stained for CD31. (A) Neo-angiogenic vessels (neo-vessels) in the fibrous septa, black circle and venules as indicated with the black arrows (ii), were defined and captured by LCM. (i) Scale bar: 15 μm, (ii) Scale bar: 30 μm. (B) RNA was isolated from endothelial cells in either venules or neo-vessels (Neo) from three patients (a, b, c). Expression levels of miR-27a were quantified by qRT-PCR and normalized to miR-520d*. Data represents the mean of quadruplicate qRT-PCR reactions±SEM. * $p<0.05$ Venules vs. Neo.

Figure 5:
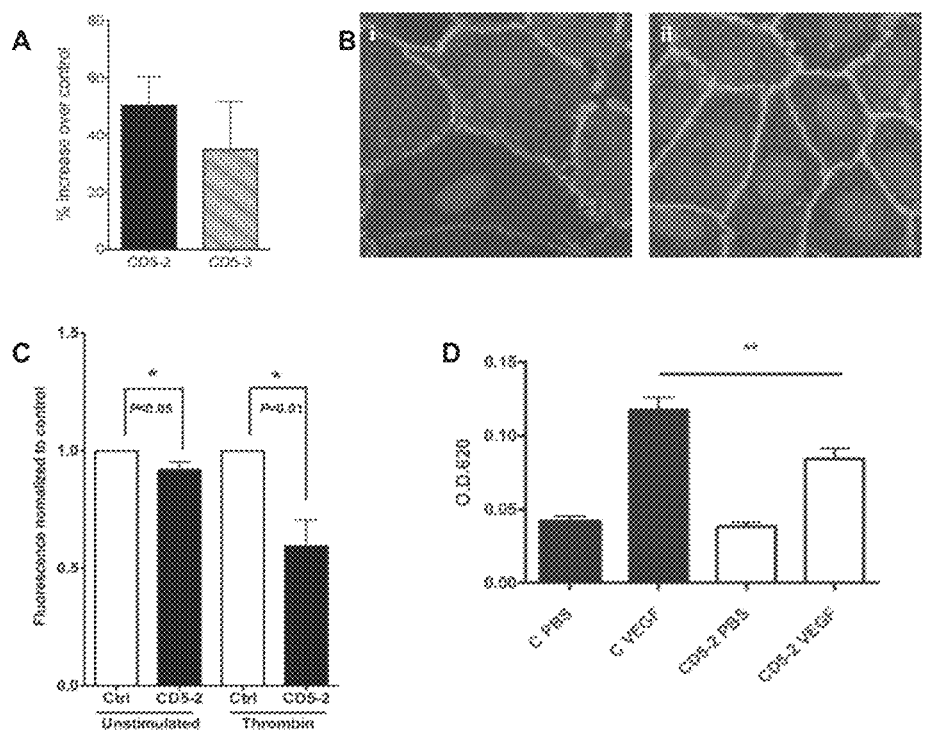

FIG. 5. Blockmirs regulate VE-cadherin Dependent Functions.

(A) VE-cadherin levels in Blockmir CD5-2 or CD5-3 transfected cells as determined by Western Blot were quantified and normalized to levels in control Blockmir transfected cells. Results show % increase over control for n=4 independent endothelial cell lines. (B) HUVEC were stained for VE-cadherin, 48 hrs after transfection. Control (i) or (ii) Blockmir CD5-2. (C) Permeability through unstimulated or thrombin stimulated monolayers of control or Blockmir CD5-2 transfected cells. Results are normalized to permeability of control, Mean+/−SEM of 3-5 experiments. (D) The Miles assay was performed with control (black) or Blockmir CD5-2 (white bars) injected intravenously. 24 hours later VEGF or PBS was given intradermally n=4 mice per group. ** $p<0.005$.

Figure 6:
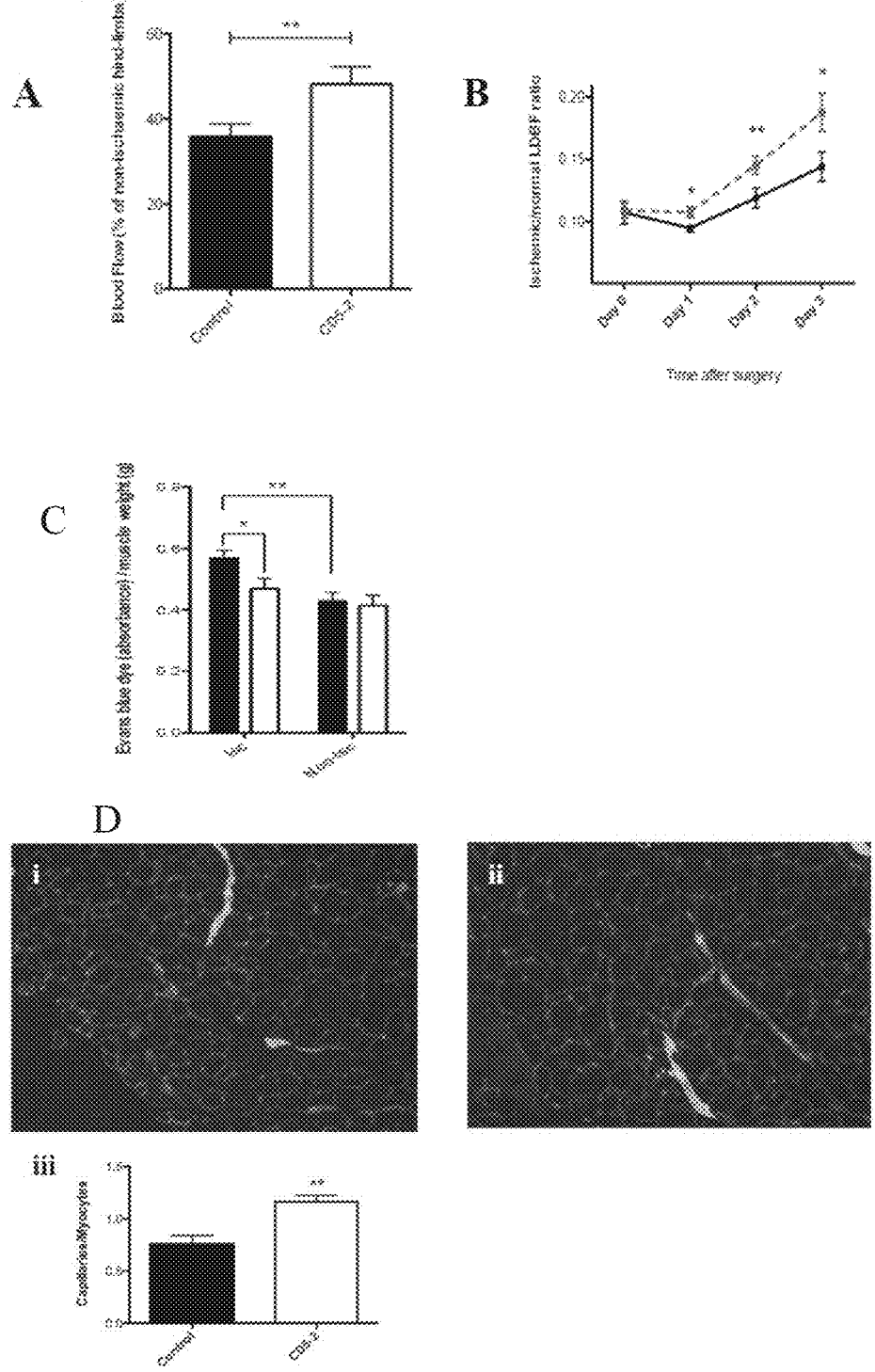

FIG. 6. Blockmirs regulate oedema and angiogenesis after ischaemia.

(A) Hind-limb blood flow were measured at times after surgery and expressed as percentage of ischaemic limb blood flow over non-ischaemic hind-limb blood flow.

*, P<0.05; **, P<0.01. n=6-10 mice per group. (B) An expanded view of the LDBF between Day0-Day3 is given in the right hand side graph. (C) Assessment of oedema 24 hours after hindlimb ischemia for mice treated with control Blockmir (black bars) and CD5-2 (white bars). The lower part of adductor muscle was taken for quantification *, p<0.05; **, p<0.01, n=8 per group. (D) Assessment of capillary density. Sections were stained for CD31. A representative area is shown for one mouse given control Blockmir (i), CD5-2 (ii), and quantification of the number of capillaries and given as the ratio of capillaries/myocytes in the ischaemic limbs (iii), n=4-5 animals. *p<0.02.

Figure 7:
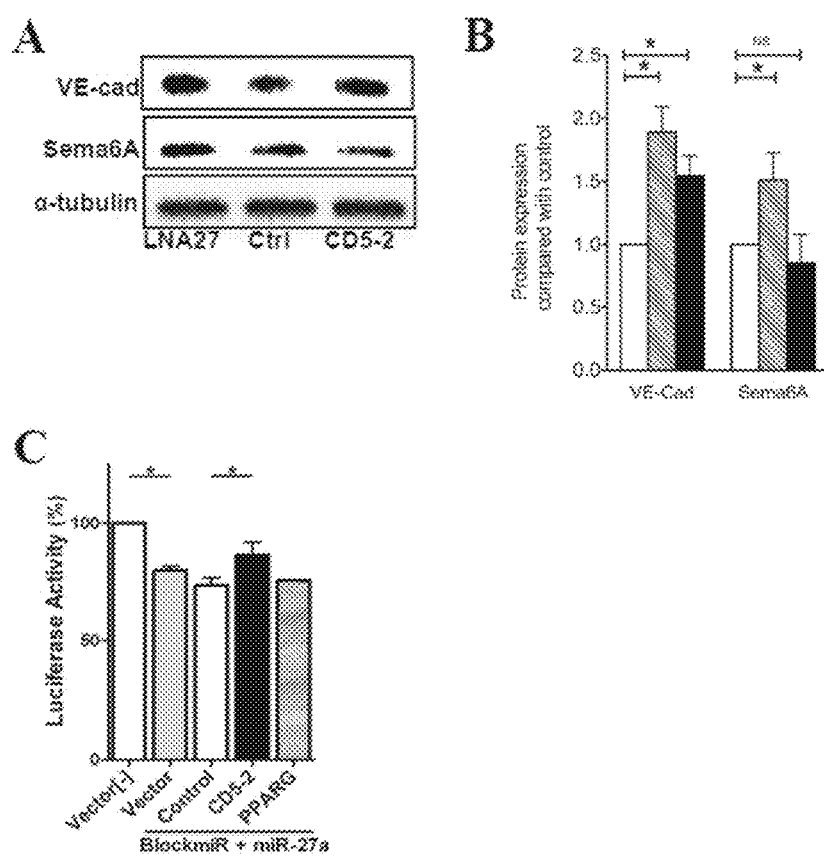

FIG. 7. Specificity of Blockmirs.

(A) Western blot analyses of VE-cadherin and Sema6A from HUVECs transfected with the LNA27, CD5-2 or control (Ctrl). Cell lysates were from HUVECs 48 h after transfection. α-tubulin used as loading control. Data represent three independent experiments. (B) Quantitative evaluation of VE-cadherin, Sema6A expression analyzed as described in (A). Control (white bar), LNA27 (black bar) and CD5-2 (stripe bar). *P<0.05 (n=3-5), NS, no significant difference relative to the control group. Mean values±s.e.m. (C) Luciferase (*Renilla*) activity from PsiCHECK2 VE-Cadherin 3'UTR (WT) in HeLa cells co-transfected with miR-27a mimic and vector only, control Blockmir, CD5-2 or Blockmir directed against miR27 binding site in PPARγ (SEQ ID NO: 10). *Renilla* luciferase activity is normalized internally to firefly luciferase expressed from the same plasmid. Luciferase activity is shown relative to that from the 3'UTR-reporter, transfected without Blockmirs and miR-27a mimic (Vector[−]), and is presented as the percentage mean±SD from three independent experiments with three replicate samples per experiment; ANOVA p<0.0001, (*) p<0.05.

Figure 8:
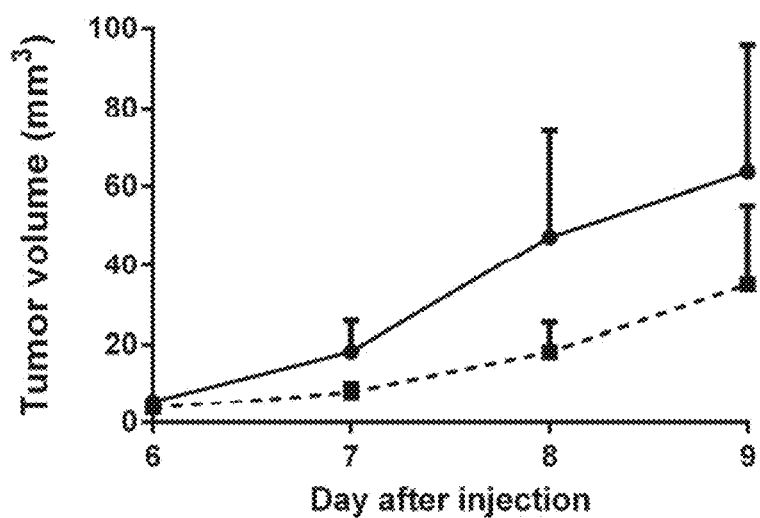

FIG. 8. Blockmirs inhibit tumour growth.

Tumour volume ($mm^3$) in C57BL/6 female mice following intravenous injection of Blockmir CD5-2 (squares) or scrambled control (circles) at 6-9 days after injection of tumour-inducing B16F10 cells into the mice. n=3 mice per group.

The subject specification contains amino acid and nucleotide sequence information prepared using the programme PatentIn Version 3.4, presented herein in a Sequence Listing. Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. Specifically, the miR-27a target 'anti-seed' region in the 3'UTR of VE-cadherin (CDH5) is shown in SEQ ID NO: 1. The region of the 3'UTR of human VE-cadherin containing the miR-27a 'anti-seed' region is shown in SEQ ID NO: 2. SEQ ID NOs: 3 and 4 show the sequences of exemplary oligonucleotides. SEQ ID NOs: 5 to 10 show the sequences of oligonucleotides used in the present study as exemplified herein (see also Table 1). The mature sequence of the human miR-27a (hsa_miR-27a) is shown in SEQ ID NO: 11.

DETAILED DESCRIPTION

The articles "a" and "an" are used herein to refer to one or to more than one (i.e., to at least one) of the grammatical object of the article. By way of example, "an element" means one element or more than one element.

In the context of this specification, the term "about" is understood to refer to a range of numbers that a person of skill in the art would consider equivalent to the recited value in the context of achieving the same function or result.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

As used herein the term "oligonucleotide" refers to a single-stranded sequence of ribonucleotide or deoxyribonucleotide bases, known analogues of natural nucleotides, or mixtures thereof. An "oligonucleotide" comprises a nucleic-acid based molecule including DNA, RNA, PNA, LNA, UNA or any combination thereof. An oligonucleotide that predominantly comprises ribonucleotide bases, natural or non-natural, may be referred to as an RNA oligonucleotide. Oligonucleotides are typically short (for example less than 50 nucleotides in length) sequences that may be prepared by any suitable method, including, for example, direct chemical synthesis or cloning and restriction of appropriate sequences.

"Antisense oligonucleotides" are oligonucleotides complementary to a specific DNA or RNA sequence. Typically in the context of the present invention an antisense oligonucleotide is an RNA oligonucleotide complementary to a specific mRNA or miRNA. The antisense oligonucleotide binds to and silences or represses, partially of fully, the activity of its complementary miRNA. Not all bases in an antisense oligonucleotide need be complementary to the 'target' or miRNA sequence; the oligonucleotide need only contain sufficient complementary bases to enable the oligonucleotide to recognise the target. An oligonucleotide may also include additional bases. The antisense oligonucleotide sequence may be an unmodified ribonucleotide sequence or may be chemically modified or conjugated by a variety of means as described herein.

The term "polynucleotide" as used herein refers to a single- or double-stranded polymer of deoxyribonucleotide, ribonucleotide bases or known analogues of natural nucleotides, or mixtures thereof. A "polynucleotide" comprises a nucleic-acid based molecule including DNA, RNA, PNA, LNA, UNA or any combination thereof. The term includes reference to the specified sequence as well as to the sequence complimentary thereto, unless otherwise indicated. Polynucleotides may be chemically modified by a variety of means known to those skilled in the art. Thus a "polynucleotide" comprises a nucleic-acid based molecule including DNA, RNA, PNA, LNA, UNA or any combination thereof.

As used herein in relation to oligonucleotides and polynucleotides, the term "nucleotide" refers to a single nucleobase or monomer unit within the oligonucleotide or polynucleotide. The terms "nucleotide" and "monomer" may be used interchangeably herein. The nucleobase may be part of a DNA, RNA, INA, LNA, UNA or combination of any two or more thereof) oligonucleotide or polynucleotide. In some embodiments, the nucleobase may be a universal base. Modified nucleobases are also contemplated by the present invention, as described hereinbelow.

The term "complementary" as used in refers to the ability of two single-stranded nucleotide sequences to base pair, typically according to the Watson-Crick base pairing rules, that is, between G and C and between A and T or U. In some embodiments, G also pairs to U and vice versa to form a so-called wobble base pair. In another embodiment, the base inosine (I) may be included within an oligonucleotide of the invention. I base pairs to A, C and U. In still another embodiment, universal bases may be used. Universal bases can typically base pair to G, C, A, U and T. Often universal bases do not form hydrogen bonds with the opposing base on the other strand. In still another embodiment, a complementary sequence refers to a contiguous sequence exclusively of Watson-Crick base pairs. For two nucleotide molecules to be complementary they need not display 100% complementarity across the base pairing regions, but rather there must be sufficient complementarity to enable base pairing to occur. Thus a degree of mismatching between the sequences may be tolerated and the sequences may still be complementary. As used herein, the term "capable of base pairing with" is used interchangeably with "complementary to".

The term "substitution" as used herein refers to a nucleobase at a particular position within an oligonucleotide or polynucleotide having been substituted for another nucleobase. The substitution may be, for example, because of the presence of a single nucleotide polymorphism in the target RNA. The term substitution also encompasses deletions of nucleobases and additions of nucleobases.

The term "Blockmir" as used herein refers to a steric blocking oligonucleotide that binds to an RNA target blocking the ability of one or more miRNA species from binding to, and affecting the activity of, said target. Blockmirs are constructed so as to be incapable of recruiting cellular RNAi machinery or RNase H. Blockmirs are described, for example, in WO 2008/061537 and WO 2012/069059, the disclosures of which are incorporated herein by reference.

In the context of this specification, the term "activity" as it pertains to a polynucleotide (e.g. a DNA, mRNA or miRNA), protein or polypeptide means any one or more cellular function, action, effect or influence exerted by the polynucleotide, protein or polypeptide. For example, in the context of a mRNA, activity will typically refer to expression of the mRNA, i.e. translation into a protein or peptide. Thus, regulation of the activity of a target mRNA by an oligonucleotide as described herein may include degradation of the mRNA and/or translational regulation. Regulation of mRNA activity may also include affecting intracellular transport of the mRNA.

The term "inhibiting" and variations thereof such as "inhibition" and "inhibits" as used herein do not necessarily imply the complete inhibition of the specified event, activity or function. Rather, the inhibition may be to an extent, and/or for a time, sufficient to produce the desired effect. Inhibition may be prevention, retardation, reduction or otherwise hindrance of the event, activity or function. Such inhibition may be in magnitude and/or be temporal in nature. In particular contexts, the terms "inhibit" and "prevent", and variations thereof may be used interchangeably.

The terms "promoting" and "inducing", and variations thereof such as "promotion" and "inducement", as used herein do not necessarily imply the complete promotion or inducement of the specified event, activity or function. Rather, the promotion or inducement may be to an extent, and/or for a time, sufficient to produce the desired effect. The promotion or inducement of angiogenesis by oligonucleotides of the invention may be direct or indirect and may be in magnitude and/or be temporal in nature.

The term "RNAi machinery" as used herein refers to the cellular components necessary for the activity of siRNAs and miRNAs or for the RNAi pathway. A major component of the RNAi machinery is the RNA induced silencing complex (the RISC complex).

As used herein the term "effective amount" includes within its meaning a non-toxic but sufficient amount or dose of an agent or compound to provide the desired effect. The exact amount or dose required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

As used herein the terms "treating", "treatment", "preventing" and "prevention" refer to any and all uses which remedy a condition or symptoms, prevent the establishment of a condition or disease, or otherwise prevent, hinder, retard, or reverse the progression of a condition or disease or other undesirable symptoms in any way whatsoever. Thus the terms "treating" and "preventing" and the like are to be considered in their broadest context. For example, treatment does not necessarily imply that a patient is treated until total recovery. In conditions which display or a characterized by multiple symptoms, the treatment or prevention need not necessarily remedy, prevent, hinder, retard, or reverse all of said symptoms, but may prevent, hinder, retard, or reverse one or more of said symptoms. In the context of some disorders, methods of the present invention involve "treating" the disorder in terms of reducing or ameliorating the occurrence of a highly undesirable event associated with the disorder or an irreversible outcome of the progression of the disorder but may not of itself prevent the initial occurrence of the event or outcome. Accordingly, treatment includes amelioration of the symptoms of a particular disorder or preventing or otherwise reducing the risk of developing a particular disorder.

The term "vascular permeability-associated disease or condition" as used herein refers to any disease or condition that results from, results in, is characterised by, or otherwise associated with vascular permeability (typically excessive vascular permeability or hyperpermeability). Thus, the association between the disease or condition and vascular permeability may be direct or indirect and may be temporally and/or spatially separated. In the context of the present specification the terms vascular permeability or excessive vascular permeability and vascular leak may be used interchangeably.

The term "subject" as used herein refers to mammals and includes humans, primates, livestock animals (eg. sheep, pigs, cattle, horses, donkeys), laboratory test animals (eg. mice, rabbits, rats, guinea pigs), companion animals (eg. dogs, cats) and captive wild animals (eg. foxes, kangaroos, deer). Preferably, the mammal is human or a laboratory test animal. Even more preferably, the mammal is a human.

Disclosed and exemplified herein are oligonucleotides capable of binding to the sequence CUGUGA blocking the ability of a miRNA (such as miRNA miR-27a) to bind to said sequence and thereby inhibiting the miRNA from affecting the activity or expression of a polynucleotide comprising said sequence. Typically the sequence is present in the 3'UTR of the VE-cadherin mRNA.

Accordingly, one aspect of, the invention provides an oligonucleotide comprising a contiguous sequence complementary to at least 8 contiguous bases of an RNA sequence comprising SEQ ID NO: 2, or SEQ ID NO: 2 comprising 1, 2 or 3 substitutions, wherein the oligonucleotide inhibits the binding of miR-27a, a variant thereof or a miRNA comprising a seed region comprising the sequence UCACAG, to said RNA.

Also provided are compositions and methods for modulating the activity of VE-cadherin in a cell using oligonucleotides as disclosed herein.

Moreover, the oligonucleotides disclosed herein also find therapeutic application. As exemplified herein, miR-27a regulates endothelial cell junctions to control vascular integrity. Inhibition of miR-27a or its specific interaction with VE cadherin inhibits vascular leak in the absence of angiogenesis. Since vascular leak is a chief pathophysiological mechanism of many vascular, inflammatory and neoplastic diseases, the study described and exemplified herein offers new opportunities for anti-vascular permeability therapies.

Accordingly also provided are compositions and methods for inhibiting or reducing vascular permeability in a vascular vessel, compositions and methods for treating or preventing a vascular permeability-associated disease or condition, compositions and methods for treating and/or enhancing recovery from ischaemic injury, compositions and methods for treating surgical wounds and promoting post-operative recovery, compositions and methods for promoting or inducing angiogenesis, compositions and methods for treating oedema, and compositions and methods for inhibiting tumour growth, using oligonucleotides as disclosed herein.

Oligonucleotides of the present disclosure also find application as research tools in medical and biological research activities, including as components of kits, facilitating investigations into, for example, VE-cadherin activity, vascular permeability and angiogenesis and potential treatments and therapies therefor.

Typically, the miRNA comprising the seed sequence UCACAG is miR-27a. The nucleotide sequence of mature human miR-27a (hsa-miR-27a) is provided in SEQ ID NO: 11. Additional sequence information for the miR-27a miRNA can be found at http://microrna.sanqer.ac.uk/sequences/index.shtml. Also contemplated herein are variants of this miRNA. Variants include nucleotide sequences that are substantially similar to sequence of miR-27a. For example, a variant miRNA may comprise a sequence displaying at least 80%, 85%, 90%, 91%, 92%, 93%, 94%, 95%, 96%, 97%, 98% or 99% sequence identity to SEQ ID NO:10.

Oligonucleotides

Oligonucleotides of the present invention typically comprises a contiguous sequence complementary to a sequence selected from the group consisting of at least about 9 contiguous bases, at least about 10 contiguous bases, at least about 11 contiguous bases, at least about 12 contiguous bases, at least about 13 contiguous bases, at least about 14 contiguous bases, at least about 15 contiguous base's, at least about 16 contiguous bases, at least about 17 contiguous bases, at least about 18 contiguous bases, at least about 19 contiguous bases, at least about 20 contiguous bases, at least about 22 contiguous bases, at least about 25 contiguous bases, at least about 30 contiguous bases, and at least about 35 contiguous bases of the sequence set forth in SEQ ID NO: 2 or the sequence of SEQ ID NO: 2 comprising 1, 2 or 3 substitutions.

In an embodiment, an oligonucleotide of the present invention may comprise a contiguous sequence complementary to a sequence selected from the group consisting of no more than 8 contiguous bases, no more than 9 contiguous bases, no more than 10 contiguous bases, no more than 11 contiguous bases, no more than 12 contiguous bases, no more than 13 contiguous bases, no more than 14 contiguous bases, no more than 15 contiguous bases, no more than 16 contiguous bases, no more than 17 contiguous bases, no more than 18 contiguous bases, no more than 19 contiguous bases, no more than 20 contiguous bases, no more than 22 contiguous bases, no more than 25 contiguous bases, no more than 30 contiguous bases, and no more than 35 contiguous bases of the sequence set forth in SEQ ID NO: 2 or the sequence of SEQ ID NO: 2 comprising 1, 2 or 3 substitutions.

In another embodiment, an oligonucleotide of the invention may comprise a contiguous sequence complementary to a sequence selected from the group consisting of 8 contiguous bases, 9 contiguous bases, 10 contiguous bases, 11 contiguous bases, 12 contiguous bases, 13 contiguous bases, 14 contiguous bases, 15 contiguous bases, 16 contiguous bases, 17 contiguous bases, 18 contiguous bases, 19 contiguous bases, 20 contiguous bases, 21 contiguous bases, 22 contiguous bases, 23 contiguous bases, 24 contiguous bases, 25 contiguous bases, 30 contiguous bases, and 35 contiguous bases of the sequence set forth in SEQ ID NO: 2 or the sequence of SEQ ID NO: 2 comprising 1, 2 or 3 substitutions.

Typically the oligonucleotide binds to positions 22-27 of SEQ ID NO: 2, this region representing the complement of the seed sequence of miR-27a, being the target site for miR-27a binding to the 3'UTR of the VE-cadherin mRNA (the 'anti-seed' region). Base pairing between the oligonucleotide and SEQ ID NO: 2 may include positions 8-28, 8-27, 9-27, 10-27, 11-27, 12-27, 13-27, 14-27, 15-27, 16-27, 17-27, 18-27, 19-27, 20-27, 21-27, 9-28, 10-28, 11-28, 12-28, 13-28, 14-28, 15-28, 16-28, 17-28, 18-28, 19-28, 20-28 or 21-28 of SEQ ID NO: 2.

In one embodiment, base pairing between the oligonucleotide and the sequence of SEQ ID NO: 2 ends at position 27 of SEQ ID NO: 2. In other embodiments, base pairing may end at position 28, 29, 30, 31, 32 or 33 of SEQ ID NO: 2. In another embodiment, base pairing between the oligonucleotide and the sequence of SEQ ID NO: 2 begins at position 22 of SEQ ID NO: 2. In other embodiments, base pairing may start at position 21, 20, 19, 18, 17, 16, 15, 14, 13, 12, 11, 10, 9, 8, 7, 6 or 5 of SEQ ID NO: 2.

Those skilled in the art will appreciate that oligonucleotides of the invention may be of any suitable length depending on the precise function or use of oligonucleotide. Typically, the oligonucleotides are between 8 and 25 bases in lengths. Even more typically, the oligonucleotides are between 10 and 20 bases in length.

For strong binding to its target RNA, the length of an oligonucleotide may be increased. In some cases, delivery into cells may be improved may using shorter oligonucleotides. Further, in other cases, the position of the oligonucleotide respectively to the anti-seed sequence of the target RNA may be adjusted. For example, the position of bases complementary to position 22-27 of the target RNA of SEQ ID NO: 2 may be adjusted such that they are placed for example at the 5'end of the oligonucleotide, at the 3'end of the oligonucleotide or in or towards the middle of the oligonucleotide. Typically, the position of bases complementary to positions 22-27 are placed in the oligonucleotide such that they start at position 1, position 2, position 3, position 4, position 5 or position 6, or at a position upstream of position 2, position 3, position 4, position 5 or position 6 or at a position downstream of position 1, position 2, position 3, position 4, position 5 or position 6, wherein the positions are counted from the 5'end of the oligonucleotide.

In some embodiments, the target RNA sequence, for example the sequence of SEQ ID NO: 2 may comprise 1, 2 or 3 substitutions. Alternatively, the sequence may comprise no substitutions. Where substitutions are present, these may be located in the region of complementarity between the oligonucleotide and the target RNA. Substitutions may be single nucleotide polymorphisms (SNPs) that may enhance or decrease miRNA regulation of the given target RNA. An SNP may create a new miRNA target site so as to cause aberrant miRNA regulation of the given target RNA. RNA editing may also give rise to substitutions.

Oligonucleotides of the invention may be capable of activating RNase H. RNase H cleaves the RNA part of a RNA-DNA duplex and the structural requirements for RNase H activation are well-known to the skilled addressee. Similarly, oligonucleotides of the invention may be capable of recruiting the cellular RNAi machinery and directing the RNAi machinery to the target RNA. This may result in cleavage of the target RNA or translational repression of the target RNA.

However in particular embodiments of the present invention, the oligonucleotides can neither recruit the RNAi machinery nor RNase H. Thus typically, oligonucleotides of the invention are capable of blocking the activity of the RNAi machinery at a particular target RNA. The oligonucleotides may do so by sequestering the target sequence (the miRNA binding site) of the target RNA, such that the RNAi machinery will not recognize the target sequence. Oligonucleotides of the invention with this activity may also be referred to as Blockmirs, because they block the regulatory activity of a given miRNA at a particular miRNA binding site in target RNA. To achieve the ability to prevent recruitment or activation of RNase H by oligonucleotides of the invention, the oligonucleotides typically do not comprise 5 or more contiguous DNA nucleobases.

The oligonucleotides of the present invention described herein and for use in accordance with aspects and embodiments disclosed herein may comprise a variety of sequence and structural modifications, depending on the use and function of the oligonucleotide, as will be described further below. Those skilled in the art will appreciate that the sequence and structural modifications described herein are exemplary only, and the scope of the present invention should not be limited by reference to those modifications, but rather additional modifications known to those skilled in the art may also be employed provided the oligonucleotide retains the desired function or activity.

By way of example only, the oligonucleotide sequence may be modified by the addition of one or more phosphorothioate (for example phosphoromonothioate or phosphorodithioate) linkages between residues in the sequence, or the inclusion of one or morpholine rings into the backbone. Alternative non-phosphate linkages between residues include phosphonate, hydroxlamine, hydroxylhydrazinyl, amide and carbamate linkages, methylphosphonates, phosphorothiolates, phosphoramidates or boron derivatives. The nucleotide residues present in the oligonucleotide may be naturally occurring nucleotides or may be modified nucleotides. Suitable modified nucleotides include 2'-O-methyl nucleotides, 2'-O-flouro nucleotides, 2'-O-methoxyethyl nucleotides, universal nucleobases such as 5-nitro-indole; LNA, UNA, PNA and INA nucleobases, 2'-deoxy-2'-fluoro-arabinonucleic acid (FANA) and arabinonucleic acid (ANA). The ribose sugar moiety that occurs naturally in ribonucleosides may be replaced, for example with a hexose sugar, polycyclic heteroalkyl ring, or cyclohexenyl group. Alternatively, or in addition, the oligonucleotide sequence may be conjugated to one or more suitable chemical moieties at one or both ends. For example, the oligonucleotide may be conjugated to cholesterol via a suitable linkage such as a hydroxyprolinol linkage at the 3' end.

Particular modifications of interest include those that increase the affinity of the oligonucleotide for complementary sequences, i.e. increases the melting temperature of the oligonucleotide base paired to a complementary sequence, or increase the biostability of the oligonucleotide. Such modifications include 2'-O-flouro, 2'-O-methyl, 2'-O-methoxyethyl groups. The use of LNA, UNA, PNA and INA monomers are also typically employed. For shorter oligonucleotides, typically a higher percentage of affinity increasing modifications are present. If the oligonucleotide is less than 12 or 10 nucleobases in length, it may be composed entirely of affinity increasing units, e.g. LNA monomers, UNA monomers or 2'-O-methyl RNA nucleobases.

In particular embodiments, the fraction of monomers in an oligonucleotide modified at either the base or sugar relatively to the monomers not modified at either the base or sugar may be less than 99%, less than 95%, less than 90%, less than 85%, less than 75%, less than 70%, less than 65%, less than 60%, less than 50%, less than 45%, less than 40%, less than 35%, less than 30%, less than 25%, less than 20%, less than 15%, less than 10%, less than 5%, less than 1%, more than 99%, more than 95%, more than 90%, more than 85%, more than 75%, more than 70%, more than 65%, more than 60%, more than 50%, more than 45%, more than 40%, more than 35%, more than 30%, more than 25%, more than 20%, more than 15%, more than 10%, and more than 5% or more than 1%.

Lipids and/or peptides may also be conjugated to the oligonucleotides. Such conjugation may both improve bioavailability and prevent the oligonucleotide from activating RNase H and/or recruiting the RNAi machinery. Conjugation of larger bulkier moieties is typically done at the central part of the oligonucleotide, e.g. at any of the most central 5 monomers. Alternatively, at one of the bases complementary to one of position 22-27 of any of SEQ ID NO: 1-5. In yet another embodiment, the moiety may be conjugated at the 5'end or the 3'end of the oligonucleotide. One exemplary hydrophobic moiety is a cholesterol moiety that may be conjugated to the oligonucleotide preventing the oligonucleotide from recruiting the RNAi machinery and improving bioavailability of the oligonucleotide. For example, the cholesterol moiety may be conjugated to one or more of the nucleobases complementary to positions 22-27 of the sequence of SEQ ID NO: 2, at the 3'end of the oligonucleotide, or at the 5'end of the oligonucleotide.

Different modifications may be placed at different positions within the oligonucleotide to prevent the oligonucleotide from activating RNase H and/or being capable of recruiting the RNAi machinery.

In a particular embodiment, phosphorothioate internucleotide linkages may connect the monomers in an oligonucleotide to improve the biostability of the oligonucleotide. All linkages of the oligonucleotide may be phosphorothioate linkages. In another embodiment, the fraction of phosphorothioate linkages may be less than 95%, less than 90%, less than 85%, less than 80%, less than 75%, less than 70%, less than 65%, less than 60%, less than 50%, more than 95%, more than 90%, more than 85%, more than 80%, more than 75%, more than 70%, more than 65%, more than 60% and more than 50%.

In an embodiment, the oligonucleotide May not comprise any RNA nucleobases. This may assist in preventing the oligonucleotide from being capable of recruiting the RNAi machinery increasing biostability of the oligonucleotide. For example, the oligonucleotide may consist of LNA and DNA nucleobases and these may be connected by phosphorothioate linkages as outlined above. In alternative embodiments, the oligonucleotide does not comprise any DNA nucleobases. In alternative embodiments, the oligonucleotide does not comprise any morpholino and/or LNA nucleobases.

In an embodiment, the oligonucleotide may comprise a mix of DNA nucleobases and RNA nucleobases to prevent the oligonucleotide from activating RNase H and prevent the oligonucleotide from recruiting the RNAi machinery. For example, DNA and RNA nucleobases may be alternated along the length of the oligonucleotide, or alternatively one or more DNA nucleobases may be located adjacent one another and one or more RNA nucleobases may be located adjacent one another.

In another particular embodiment, the oligonucleotide comprises a mix of LNA monomers and 2'-O-methyl RNA nucleobases. As above, LNA and 2'-O-methyl RNA nucleobases may be alternated along the length of the oligonucleotide, or alternatively one or more LNA nucleobases may be located adjacent one another and one or more 2'-O-methyl RNA nucleobases may be located adjacent one another.

In some embodiments, the number of nucleobases present in a oligonucleotide that increase the affinity of the oligonucleotide for complementary sequences is at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, or at least 22 nucleobases. In some embodiments, the the number of nucleobases present in a oligonucleotide that increase the affinity of the oligonucleotide for complementary sequences is 1, 2, 3, 4, 5, 6, 7, 8, 9, 10, 11, 12, 13, 14, 15, 16, 17, 18, 19, 20, 21, and 22 nucleobases.

In particular embodiments, the nucleobases that increase the affinity of the oligonucleotide for complementary sequences may be located at the flanks of the oligonucleotide, i.e. at or near either or both of the 5' and 3' ends of the oligonucleotide, or may be located at or near the centre of the oligonucleotide. The nucleobases that increase the affinity of the oligonucleotide for complementary sequences may also be distributed evenly across the length of the oligonucleotide.

In particular exemplary embodiments, the oligonucleotide has a sequence as set forth in one of SEQ ID NO: 5, SEQ ID NO: 6, and SEQ ID NO: 7.

VE-Cadherin Activity and Therapeutic Indications

By virtue of the ability of oligonucleotides of the present invention to inhibit the binding of miR-27a, a variant thereof or a miRNA comprising a seed region comprising the sequence UCACAG, to target RNA, an aspect of the invention provides a method for modulating the activity of VE-cadherin in a cell, the method comprising contacting the cell with an effective amount of an oligonucleotide of the invention to thereby modulate the activity of the VE-cadherin.

The step of contacting the cell with the oligonucleotide may occur in vitro, ex vivo or in vivo. The cell may be present in a biological sample obtained from a subject.

Another aspect of the invention provides a method for inhibiting or reducing vascular permeability in a subject in need of such treatment, the method comprising administering to the subject an effective amount of an oligonucleotide of the invention.

Another aspect of the invention provides a method for treating or preventing a vascular permeability-associated disease or condition in a subject, the method comprising administering to the subject an effective amount of an oligonucleotide of the invention.

Another aspect of the invention provides a method for treating and/or enhancing recovery from ischaemic injury, the method comprising administering to a subject in need of such treatment an effective amount of an oligonucleotide of the invention.

Vascular permeability-associated diseases and conditions to which embodiments of the invention relate include, but are not necessarily limited to, oedema, cardiovascular disease, myocardial infarction, peripheral vascular disease, ischaemia, stroke, cancer, atherosclerosis, psoriasis, diabetes, autoimmune diseases such as rheumatoid arthritis, thrombocytopenia, altitude sickness, barotrauma, iatrogenic disorders, bacterial infections, viral infections, and ocular conditions associated with vascular leak such as non-proliferative and proliferative retinopathies (including diabetic retinopathy), macular oedema (including diabetic macular oedema), glaucoma and macular degeneration (including age-related macular degeneration). The oedema may be generalised oedema or localized or organ-specific oedema. The oedema may be, for example, cardiac oedema, pulmonary oedema, renal oedema, macular oedema, cerebral oedema, malnutritional oedema or lymphoedema. The oedema may result from a surgical procedure, in particular a major surgical procedure, such as cardiac surgery, organ transplantation surgery, knee and hip replacement surgery, dental surgery or limb amputation surgery (for example associated with diabetic complications).

Another aspect of the invention provides a method for inhibiting tumour growth, the method comprising administering to a subject in need of such treatment an effective amount of an oligonucleotide of the invention.

Embodiments of the invention disclosed herein also provide for the promotion or inducement of angiogenesis in cells and tissues using oligonucleotides of the invention, which promotion or inducement may occur in vivo or ex vivo. By way of non-limiting example, circumstances where the promotion of angiogenesis may be desired, include in wound healing (of chronic, acute and surgical wounds), in the treatment of some gynaecological disorders and infertility, in the treatment of coronary artery disease and ocular conditions, in the prevention of stroke, in tissue repair or regeneration, and tissue engineering (for example in three-dimensional scaffold constructs). Non-limiting examples of wounds that are amenable to treatment in accordance with embodiments of the invention include surgical wounds, ulcers, such as venous ulcers and diabetic ulcers, burns and other forms of tissue trauma. Particular embodiments of the invention relate to the treatment of surgical wounds and to the promotion of post-operative recovery. The surgical wound amenable to treatment may be any wound resulting from surgery or induced in the course of surgery including, for example, those associated with dental surgery, cardiac surgery, organ transplantation surgery, knee and hip replacement surgery—and limb amputations (for example associated with diabetic complications).

Pharmaceutical Compositions

Oligonucleotides of the present invention may be administered in accordance with the embodiments disclosed herein in the form of pharmaceutical compositions, which compositions may comprise one or more pharmaceutically acceptable carriers, excipients or diluents. Such compositions may be administered in any convenient or suitable route such as by parenteral (e.g. subcutaneous, intraarterial, intravenous, intramuscular), oral (including sublingual), nasal or topical routes. In circumstances where it is required that appropriate concentrations of the oligonucleotide are delivered directly to the site in the body to be treated, administration may be regional rather than systemic. Regional administration provides the capability of delivering very high local concentrations of the oligonucleotide to the required site and thus is suitable for achieving the desired therapeutic or preventative effect whilst avoiding exposure of other organs of the body to the compound and thereby potentially reducing side effects.

It will be understood that the specific dose level of a composition of the invention for any particular individual will depend upon a variety of factors including, for example, the activity of the specific oligonucleotide(s) employed, the age, body weight, general health and diet of the individual to be treated, the time of administration, rate of excretion, and combination with any other treatment or therapy. Single or multiple administrations can be carried out with dose levels and pattern being selected by the treating physician. A broad range of doses may be applicable. Considering a patient, for example, from about 0.1 mg to about 1 mg of agent may be administered per kilogram of body weight per day. Dosage regimens may be adjusted to provide the optimum therapeutic response. For example, several divided doses may be administered daily, weekly, monthly or other suitable time intervals or the dose may be proportionally reduced as indicated by the exigencies of the situation.

Examples of pharmaceutically acceptable carriers or diluents are demineralised or distilled water; saline solution; vegetable based oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

Pharmaceutical forms suitable for injectable use include sterile aqueous solutions (where water soluble) or dispersions and sterile powders for the extemporaneous preparation of sterile injectable solutions or dispersions. The formulation must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filter sterilisation. Generally, dispersions are prepared by incorporating the various sterilised active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active agents are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 2000 mg of active.

Tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the oligonucleotides may be incorporated into sustained-release preparations and formulations.

The present invention contemplates combination therapies, wherein oligonucleotides as described herein are coadministered with other suitable agents that may facilitate the desired therapeutic or prophylactic outcome. For example, in the context of cancer or a tumour, one may seek to maintain ongoing anti-cancer or anti-tumour therapies such as chemotherapy or radiotherapy whilst employing oligonucleotides in accordance with embodiments of the present invention to inhibit or reduce tumour angiogenesis and/or tumour metastasis. By "coadministered" is meant simultaneous administration in the same formulation or in two different formulations via the same or different routes or sequential administration by the same or different routes. By "sequential" administration is meant a time difference of from seconds, minutes, hours or days, between the administration of the agents. Administration may be in any order.

Embodiments of the present invention also provide kits for use in accordance with the invention. For example, kits of the invention may contain one or more Blockmirs disclosed herein, and optionally scrambled oligonucleotides for use as controls. Such kits may be used, for example, in medical or biological research activities, including investigations into VE-cadherin activity, vascular permeability or angiogenesis. Kits according to the present invention may also include other components required to use the Blockmirs, such as buffers and/or diluents. The kits typically include containers for housing the various components and instructions for using the kit components in the methods of the present invention.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present invention will now be described with reference to the following specific examples, which should not be construed as in any way limiting the scope of the invention.

EXAMPLES

The following examples are illustrative of the invention and should not be construed as limiting in any way the general nature of the disclosure of the description throughout this specification.

General Methods

Cell Culture

HUVEC were isolated and cultured as previously described (Litwin et al., 1997) and used between passage two and four. HEK293T and HeLa cells were maintained in DMEM (Gibco) supplemented with 10% FBS, Oligonucleotides MicroRNA (Miridian) mimics of human miR-27a were synthesised by Dharmacon. LNA inhibitors of miR-27a (LNA-27a) were designed and synthesized by Exiqon. All Blockmirs were designed and synthesized by MirrX. Stealth RNAi™ siRNA targeting human VE-Cadherin mRNA was designed and synthesised by Invitrogen. The sequences of oligonucleotides used in the experiments described in the following examples are provided in Table 1 and in the Sequence Listing appearing at the end of the specification.

TABLE 1

| Oligonucleotide | Sequence (5'-3')[1] | SEQ ID NO |
| --- | --- | --- |
| CD5-1 | TUCACAGUTGCUUCA | 5 |
| CD5-2 | TUCACAGUTGCTTCA | 6 |
| CD5-3 | TUCACAGUTGCTTCA | 7 |
| LNA-27a antimer | CUTAGCCACUGTGAA | 8 |
| Scrambled control | TCCAGAGATGGTUGA | 9 |
| 154-pparg | TUCACAGUAAATTTC | 10 |

[1]single underlining represents an LNA monomer; double underlining represents a 2' o-methyl RNA monomer; bold represents a UNA monomer Plasmids PsiCHECK VE-Cadherin 3'UTR (WT) was prepared by cloning the entire 3'UTR derived from the human VE-cadherin gene into plasmid PsiCHECK-2 (Promega) immediately downstream of a *Renilla* luciferase reporter gene. This plasmid contains a firefly luciferase expression cassette that acts as an internal normalization of luciferase activity. PsiCHECK mut-VE-Cadherin 3'UTR (Mut) was prepared by mutating the miR-27a binding site in the VE-cadherin 3'UTR in plasmid PsiCHECK VE-Cadherin 3'UTR.

Reporter plasmids pMiR-Target, pMir.PPARG 3'UTR and pMir.SPRY2 3'UTR were prepared by Origene. pMir.PPARG 3'UTR contains the 3'UTR derived from the human Peroxisome proliferator-activated receptor gamma gene, cloned immediately downstream of the firefly luciferase reporter, while pMir.SPRY2 3'UTR is similarly constructed to carry the human Sprouty homolog 2 (*Drosophila*) 3'UTR. pMiR-Target served as an empty vector control. For transfection experiments, firefly luciferase activity from pMiR-Target, pMir.PPARG 3'UTR and pMir.SPRY2 3'UTR was normalized to *Renilla* luciferase expression from plasmid pGL4.73 (Promega) which served as a transfection control.

Transient Transfection and Luciferase Assay

HUVEC cell transfections were performed in T25 flasks using HiPerFect transfection reagent (Qiagen) according to the manufacturers instructions. Cells were seeded at $4 \times 10^5$ cells per flask and incubated for 24 hr prior to being transfected with microRNAs mimics at a final concentration of 15 nM or LNA, Blockmirs or VE-cadherin siRNAs at a final concentration of 30 nM. Cells were assayed for luciferase activity 24 h after transfection. For VE-cadherin reconstitution experiments 1 μg of the appropriate plasmid was co-transfected with miRNA mimics at a final concentration of 15 nM using the Amaxa® HUVEC Nucleofector® Kit (Lonza) according to the manufacturer's instructions.

HEK293T and HeLa cell transfections were performed in triplicate in 96-well plates using Lipofectamine 2000 according to the manufacturers instructions. Cells were plated at $6 \times 10^3$ cells per well and incubated for 24 hr prior to co-transfections involving luciferase reporter construct (70 ng), BlockmiRs or LNA (3.75 nM) and miR 27a-mimics (3.75 nM-30 nM) per well. As an internal control, plasmid pGL4.73 (0.5 ng), which contained the *Renilla* luciferase reporter gene, was co-transfected and luciferase activity quantitated using the PolarStar Omega (BMG Labtech), 24 hours later.

miRNA Microarray

Arrays were performed as previously described (Thomson et al., 2004). Competitive hybridzations were performed using RNA from two separate HUVEC cell line experiments with data from these biological replicates pooled for each time point. Arrays were scanned using a GenePix 4000B scanner driven by GenePixPro 4.0 (Molecular Devices). Analysis was performed using freely available statistical programming and graphics environment R (http://cran.r- project.org). MiRNAs which were differentially expressed were identified using the empirical Bayes approach which ranks genes on a combination of magnitude and consistency of differential expression (Smyth, 2004)

Analysis of miRNA Microarray Data

Normalization tools within the Limma (Linear Models for Microarray Data) package were used to read in and normalize the SPOT output file generated from the arrays. Generally, microarray normalization for two colour arrays involves normalizing log ratio values (M values) within each array, (within-array normalization) which may arise due to print-tip group variability, and normalizing channel intensities (A values) between the arrays. In the arrays used here, due to the small number of spots, per print-tip groups, within-array normalization was performed using the global loess method (with function 'Normalize WithinArrays'). The default quintile methods with function ('NormalizeWithinArrays') was used for between-array normalization.

Differential expression analysis was also performed in Limma, using tools for linear modeling and the empirical Bayes statistic calculations which ranks genes on a combination of magnitude and consistency of differential expression The 'toptable' function in Limma was used to provide summary statistics for each miRNA at a given timepoint including: the average fold change (M), a moderated t-statistic, p-value, p-value corrected for multiple testing and a B-statistic (Explained in more detail below).

Average log fold change (M): Represents the average $\log_2$ fold change of each microRNA across replicates at each time point contrast (e.g. 3 h vs. 0 h)

Moderated t statistic: The moderated t-statistic has the same interpretation as an ordinary t-statistic except that the standard errors have been moderated across genes, i.e., shrunk towards a common value, using a simple Bayesian model.

P value: Represents the significance of the fold change for that gene at the given time point. This can be adjusted for multiple testing providing the adjusted p-statistic. The Benjamini-Hochberg correction was used for the adjustment.

B statistic: Represents the log (base exp) odds of probability of expression vs. probability of non-expression.

RNA Extraction and qRT-PCR

Total RNA was isolated from HUVEC by Trizol extraction (Invitrogen) according to the manufacturer's instructions. Complementary DNA was randomly primed from 1 μg of total DNAse-treated RNA using the High Capacity cDNA Reverse Transcription Kit (Applied Biosystems). For analysis of miRNA expression, cDNA synthesis was performed using the TaqMan® MicroRNA Reverse Transcription Kit (Applied Biosystems) using TaqMan® MicroRNA assays according to the manufacturer's instructions (Applied Biosystems).

Matrigel Tube Formation Assay

The Matrigel assay was performed as previously described (Gamble et al., 1993). Briefly, according to the manufacturers' instructions, Matrigel (Becton Dickinson) was thawed and 100 μl of Matrigel was added to a flat bottom 96 well plate which was allowed to polymerize at 37° C. for 1 hour. HUVEC were then plated at $3.6 \times 10^4$ cells per well in HUVEC medium. Photographs were taken at regular intervals over 24 h.

Permeability Assay

The permeability assay was performed as previously described (Gamble et al., 2000). Briefly, 24 h post transfection HUVEC were plated at $1 \times 10^5$ cells per transwell (Corning) for 24 h in HUVEC medium and then in 2% FCS HUVEC medium for a further 24 h. FITC-conjugated dextran (2 μg) was added to the upper chamber of all wells. The amount of FITC-dextran in the lower chambers of the transwells was determined using a LS 50B Luminescence Spectrometer (Perkin Elmer) at an excitation wavelength of 485 nm and emission wavelength of 530 nm. Permeability is given as the amount of FITC-dextran passing from the upper chamber to the lower chamber. HUVEC overexpressing miR-27a were plated on to transwells. 24 h after the transfection procedure and treated in the same manner as cells transfected with a control mimic.

Immunoblotting

HUVEC were lysed in ice-cold lysis buffer (1M Tris.HCl, pH 7.5, with 1% NP-40, 5M NaCl, 200 mM EGTA, 500 mM NaF, 100 mM $Na_4P_2O_7$ and protease inhibitor cocktail). Protein concentrations were assayed using Bradford Reagent (BioRad). Equal amounts of protein were loaded onto an acrylamide gel, separated by SDS-PAGE, transferred to PVDF membrane, blocked with 5% skim milk powder in PBS-T and probed with a VE-cadherin primary antibody (C-19, Santa Cruz) and subsequently with an appropriate secondary antibody. After washing, reactive bands were detected by chemiluminescence (Amersham 8 Pharmacia Biotech). Membranes were washed and re-probed using a monoclonal anti-β actin antibody (Sigma) as a loading control.

VE-Cadherin Localization

Localization studies were performed as described (Li et al., 2009) using cells plated in LabTek slides (In vitro technologies) for 48 h. Localization of VE-cadherin was viewed using a 40× objective on a Nikon Eclipse Ti-U Inverted Microscope (Nikon) equipped with excitation filters for fluorescein and acquired to a Digital Sight cooled colour digital camera (Nikon). Images were adjusted for brightness and contrast using NIS-AR advanced research software (Nikon).

Collagen Assay

The collagen capillary tube formation assay was performed as previously described (Gamble et al., 1993) Capillary tube formation was stimulated by the addition of 20 ng/ml phorbol myristate acetate (PMA) and an antibody against $\alpha_2\beta_3$-integrin (AC11), which promotes the formation of complex multicellular tubes.

Matrigel Plug Assay

The Matrigel plug assay was performed as previously described (Zhang et al., 2006). Six to eight week-old female C57BL/6 mice were injected subcutaneously (right flanks) with 500 μl of Matrigel containing FGF-2 (0.5 μg, (Sigma, MI), 90 μg control or miR-27a mimic, or no mimic (vehicle) and FuGENE6 (2.5 μl). 14 days later, plugs were resected and fixed in 10% paraformaldehyde. 5 μm cross-sections were stained with Haematoxylin-Eosin. Erythrocyte-containing vessels in the plugs was quantified by light microscopy under 100× magnification and expressed as the mean of three random fields. Images were acquired at room temperature using a UplanFl 20×/0.50 objective for panel A and UPlanFl 40×/0.77 objective for panel B on a BX51 microscope to a DP70 camera using DPC Controller 3.1.1.267 software (all from Olympus). Subsequent to data acquisition, ImageJ (NIH) was used to make luminosity and contrast adjustments. Experiments were carried out on two separate days using two separate batches of miRNA mimics.

Laser Capture

Excision of endothelial cells from the Svenules and neo-angiogenic vessels was achieved using the Arcturus PixCell IIe instrument. Laser diameter was set to 7.5 μM and laser pulse set at 0.2 seconds. Endothelial cells were transferred onto a CapSure Macro LCM Caps. Approximately five to ten LCM caps were collected per patient for the two endothelial cell populations. Images were acquired at room temperature using UPlanFi 4×/0.13, UPlanFi 10×/0.30, LCPlanFl 20×/0.40 objectives on a Arcturus PixCell IIe microscope (Molecular Devices) and acquired to a Hitachi ½ inch single chip CCD colour camera (Hitachi). Images were adjusted for brightness and contrast using LCM ver. 2.0 software.

Miles Assay for In Vivo Permeability

The Miles assay was performed as an in vivo model of permeability essentially as previously described (Li et al., 2008). Intradermal injections into the back were performed on 8 week-old C57BL/6J-Tyr$^{c-2J}$/J mice, with 4 μg of the control LNA or miR-27a LNA injected. The following day, 100 μl of 5% Evans blue dye was injected intravenously, then 15 minutes later PBS or 10 ug of VEGF was injected intradermally into the same site as the LNA and mice were sacrificed 30 mins later. Permeability was measured as the extent of blue dye perfusion away from the injection site. For quantification, a biopsy of the affected area was taken, the dye eluted in formamide overnight at 56° C., and the absorbance read at 620 nm. A total of 9 mice were used. Experiments were carried out on two different days.

Mouse Model of Unilateral Hind-Limb Ischaemia

The entire left femoral artery and vein were ligated and excised surgically from wild-type C57BL/6 mice (Egami et al., 2006). Blockmirs were injected systemically via the tail-vein at a dose of 30 mg per kg of body weight. Hind-limb blood flow was measured using high-definition Laser Doppler imager (Moor Instruments UK). Laser Doppler Blood flow (LDBF) measurements was taken at different time points on both left and right hind-limb (pre-surgery, Day 0, 1, 2, 3, 7 and 10). During laser scanning, mice anaesthetized with methoxyflurane and were placed on a heating pad (37° C.) to minimize variations due to body temperature. The hind-limbs were scanned a minimum of three repetitive scans. The percentage of the ischaemic (left) over sham (right) hind-limb blood flow was calculated and averaged.

Permeability Assay Using the Hind-Limb Ischaemia Model

Eight animals in each group were injected intravenously with 0.5% Evans Blue (200 μl) 24 hours post-surgery and treatment with blockmirs. The dye was allowed to circulate for 30 minutes before the mice were sacrificed. The adductor group muscle was excised and weighed. Evans Blue in tissues was extracted with formamide for 24 hours at 55° C., and its fluorescence at 620 nm were measured using LabSystem Multiskan and MultiSoft plate reader. Vascular permeability was expressed as the levels of dye leakage in absorbance per weight of muscle in grams.

Determination of the Capillary Density

Mice were anaesthetized with methoxyflurane and approximately 1 mL of blood was collected from the heart by cardiac puncture. Next, the mice were euthanized by cervical dislocation. Medial thigh adductor muscles of ischemic and non-ischemic limbs were harvested and processed as frozen sections of 8 μm-thickness. The sections were fixed in ice-cold acetone for 10 minutes and stained with a cocktail of antibodies including rat anti-mouse Laminin (1:1000, Abcam), anti-CD31 conjugated to phycoerythrin (1:200, Abcam) and anti-smooth muscle actin conjugated to FITC (1:500, Abcam). The sections were washed and stained with secondary anti-rat conjugated to Alexa Fluor dye 350 (1:2000, Invitrogen Molecular Probes). 10 different random microscopic fields at 200× magnification (Olympus LUCPLFLN 20× objective, NA 0.45) were taken from of each animal using Olympus IX71 microscope and Olympus DP71 camera. The acquisition software consists of DP Controller (version 3.1.1.267) and DP Manager (3.1.1.208) both from Olympus. The images were analysed using ImageJ version 1.46a software. Capillary density was expressed as number of capillaries per number of myocytes.

Statistics

Unless otherwise stated the T-test was performed.

Ethics

Human Ethics approval was obtained from the Royal Prince Alfred Hospital, Sydney, Australia and Animal Ethics approval was obtained from the Animal Ethics Committee of either The University of Sydney or University of NSW.

Example 1

Identification of Regulated miRNAs During In Vitro Angiogenesis

A miRNA microarray was used to identify microRNAs regulated during capillary tube formation. Results demonstrated 33 upregulated and 69 downregulated miRNAs during the process, based on positive B and M-values. Potential targets of the most highly regulated miRNAs and which are involved in regulation of permeability were investigated using web-based target prediction algorithms including TargetScan, PicTar and miRanda. Of particular interest was miR-27a, predicted to target VE-cadherin, the endothelial specific calcium-dependent cell adhesion molecule, responsible for cell-cell interactions and adhesion in solid tissues and for VEGF-mediated signaling. The 3'UTR of VE-cadherin contains a single predicted 8-mer site for miR-27a with an exact match at positions 2-8 of the mature miRNA followed by an 'A' (the seed region+position 8). The miRNA microarray expression profile of miR-27a, and the 2 other members of this miRNA cluster, miR-23a and miR-24 was confirmed by qRT-PCR, using a pool of a further three independent HUVEC lines (data not shown).

Example 2

MiR-27a Alters VE-Cadherin Expression and VE-Cadherin Dependent Function

Figure 1:
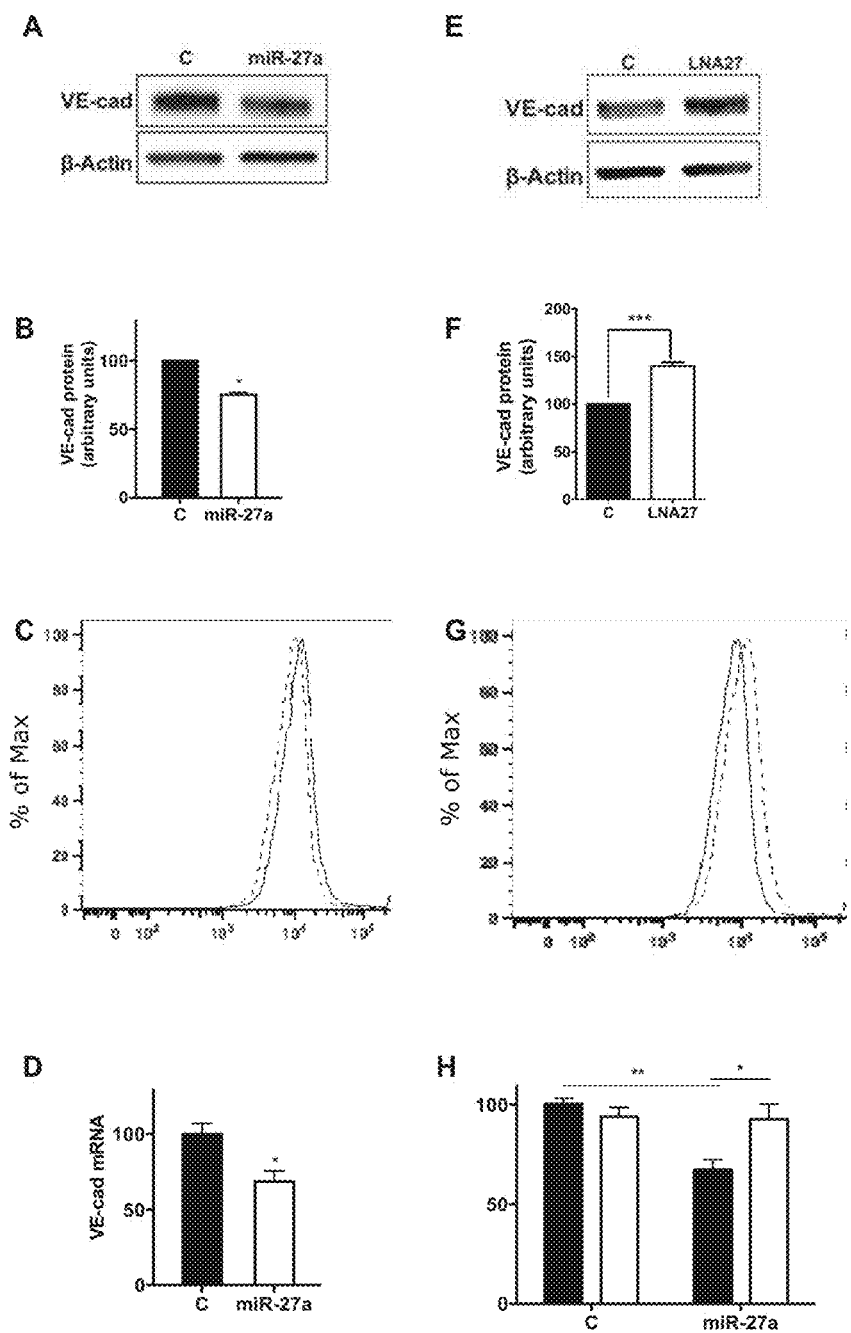
FIG. 1. miR-27a Targets VE-cadherin.

To determine whether miR-27a regulates VE-cadherin expression, VE-cadherin protein levels were measured in miR-27a-mimic transfected cells. There was a significant decrease (25%+/−4%, n=5) in VE-cadherin protein expression (FIGS. 1A and 1B), a decrease of similar magnitude in cell surface expression as analysed by flow cytometry (FIG. 1C) and mRNA (by 31%+/−7%, n=5) (FIG. 1D). Conversely, knockdown of miR-27 using an anti-miR-27a antimer containing locked nucleic acids (LNA) (LNA-27a; SEQ ID NO:8) resulted in an upregulation (22%+/−4%) of VE-cadherin protein expression (FIGS. 1E and 1F) and cell surface expression (FIG. 1G).

Ectopic expression of miR-27a in HEK293T cells suppressed luciferase activity (33%+/−3%, n=4) when a luciferase reporter plasmid containing the entire 3'UTR of VE-cadherin was co-transfected into HEK293T cells. Mutation of the miRNA site was able to reverse the repression of luciferase activity (FIG. 1H) confirming the direct interaction between miR-27a and the miR-27a binding site in the 3'UTR of VE-cadherin.

The effect of miR-27a overexpression (miR-27a mimic) was tested in settings where VE-cadherin is known to be critically involved. miR-27a-mimics had no effect on cell viability and induced a small but significant increase on endothelial cell proliferation. In endothelial cell monolayers, cells transfected with a control mimic showed the characteristic closely apposed junctions decorated with VE-cadherin (FIG. 2Ai). In contrast, miR-27a-mimic cells had gaps between the junctions, there was a broader pattern to the staining for VE-cadherin and the cells were more flattened (FIG. 2Aii). Cells transfected with anti-miR-27a LNA also showed a change in VE-cadherin distribution. In a loosely packed monolayer the control cells showed more intercellular gaps and a broader pattern of staining (FIG. 2Bi). In contrast, anti-miR-27a cells showed more tightly apposed junctions and less intercellular gaps (FIG. 2Bii). Consistent with the disrupted junctions, the miR-27a-mimic cells showed a small but significant increase in permeability (FIG. 2C) whereas the anti-miR-27a LNA transfected cells inhibited endothelial cell permeability following stimulation with the powerful permeability inducing agent, thrombin (FIG. 2D). The anti-miR-27 LNA was also effective in vivo. FIG. 2E demonstrates that anti-miR-27a LNA significantly reduced vascular permeability to VEGF in mice and consistent with this, the LNA also inhibited endogenous miR-27a levels in the tissue (data not shown). Finally, overexpression of miR 27a mimics inhibited capillary tube formation in vitro (FIG. 3A) and angiogenesis in vivo using the Matrigel plug assay (FIG. 3B).

To confirm that VE-cadherin is a major regulator of capillary tube formation, VE-cadherin was knocked down using siRNA yielding approximate 20-30% knockdown, similar to that seen with the miR-27a mimics (data not shown). The cells remained viable but when plated onto Matrigel, the capillary tubes were thin and prone to breakage and no longer formed a stable network as occurred in the control (data not shown), a phenotype very similar to that seen with overexpression of miR-27a. A rescue experiment of the miR-27a overexpression effects was then conducted using a VE-cadherin expression plasmid. An increase of approximately 5 fold in the amount of VE-cadherin expression was achieved with this expression plasmid. VE-cadherin overexpression was able to partially reverse the effects of miR-27a-mimics in the capacity to form capillary tubes on Matrigel (FIG. 3C), When migration of EC was induced using a scratch assay, miR-27a was rapidly down-regulated while the mRNA levels of VE-cadherin were upregulated. By 24 hours after wounding, miR-27a levels were high and consistent with this the levels of VE-cadherin mRNA had decreased (FIG. 3D) as well as the protein (data not shown). Together, these results suggest that VE-cadherin is a major target of miR-27a in endothelial cells and its regulation results in the perturbed capillary tube formation Observed.

Example 3

MiR-27a is Downregulated in Neo-Vessels in Disease

The data described above would suggest that the endothelial cells in vessels undergoing a limited angiogenic response should have decreased levels of miR-27a compared to endothelial cells in mature non-angiogenic vessels. To test this hypothesis, the inventors investigated the expression of miR-27a in vessels from patients with a disease where angiogenesis is known to occur but is not associated with tumour growth. Paraffin embedded liver sections were obtained from three patients with cirrhosis. The fibrotic area surrounding the regenerative nodules is known to be a setting where new vessels form via angiogenesis (neo-vessels) and this area in normal liver is free from such neo-vessels (Medina et al., 2004). Endothelial cells from venules and neo-vessels (FIG. 4A), were collected by laser capture microdissection (LCM) and RNA was isolated from the samples. miRNA profiles, analysed using Taqman Low Density Arrays (TLDA) showed similar numbers of miRNAs were detected in the venules as in the neo-vessels in each of the three patients although there was variation in the number of miRNAs detected between patients. The average Ct value for detected miRNAs was similar between both groups and patients. In the original array screen miR-520d* was found to be highly stable and therefore was used as a normalisation control for the qRT-PCR. To address the cellular purity of the LCM sample, it was not possible to investigate levels of mRNAs specific for endothelial cells or hepatocytes due to the limitation of the amount of captured material. However, it was noted that miR-122, a highly abundant and liver-specific miRNA that accounts for 70% of the total liver miRNA population and which is undetectable in other tissues (Lagos-Quintana et al., 2002) was not detected in any of the samples, suggesting that the captured cells were not significantly contaminated by hepatocytes.

The RNA samples were then analysed by qRT-PCR for miR-27a expression and results were normalized to miR-520d* expression (FIG. 4B). For all three patients there was a significant decrease in miR-27a levels in cells from the neo-vessel population compared with cells from the venules. Thus, although the patient numbers are small, the data is supportive of the idea that downregulation of miR-27a is associated with regulated angiogenesis.

Example 4

Blockmirs to VE-Cadherin Regulate VE-Cadherin Expression miRNAs are able to target multiple genes at least partially due to the highly conserved seed sequence used in target binding. Thus, modulating miRNA activity using antagonists binding directly to miRNAs, leads to multiple target genes being deregulated, and does not indicate which target(s) is/are critical for a given function (of the miRNA). To better understand which targets of miR-27a are critical for miR-27a regulation of permeability and angiogenesis, Blockmirs were used. Blockmirs are steric antisense oligonucleotide blockers that bind to specific miRNA binding sites in target RNAs thereby preventing miRNA binding to the target site. The Blockmirs used in the present study were designed as 15-mer LNA/2'-O-methyl oligonucleotides complementary to the miR-27a binding site in VE-cadherin mRNA, designated CD5-1 (SEQ ID NO:5), CD5-2 (SEQ ID NO:6), and CD5-3 (SEQ ID NO:7).

Using 2 different Blockmirs, CD5-2 (SEQ ID NO:6) and CD5-3 (SEQ ID NO:7), designed to bind to the miR-27a binding site in the 3'UTR of VE-cadherin, the inventors showed that the level of VE-cadherin was significantly increased in endothelial cells (FIG. 5A). Further work was performed on the Blockmir CD5-2 as it consistently regulated VE-cadherin levels similar to that seen with the anti-miR-27a LNA. Blockmir CD5-2 also regulated VE-cadherin localization to junctions in endothelial cell monolayers (FIG. 5B), inhibited permeability to thrombin, (FIG. 5C) and inhibited VEGF induced vascular leak as measured in the Miles assay (FIG. 5D).

Example 5

Blockmirs to VE-Cadherin and Ischaemic Injury

The inventors also investigated the effect of the CD5-2 Blockmir on recovery following hind limb ischaemia in mice. miR-27a is rapidly downregulated within the first 2 days after injury, and returned to normal or slightly higher levels thereafter. Blockmir CD5-2 was given as a single systemic injection on Day 0, immediately after the induction of ischaemia. The Blockmir lead to a significant improvement in the blood flow as measured on Day 7 (FIG. 6A). Moreover, the recovery from ischaemia was evident within 24 hours (FIG. 6B). The Blockmir CD5-2 resulted in a decrease in oedema in the ischaemic muscle within the first 24 hours (FIG. 6C). Further, CD5-2 stimulated angiogenesis as assessed by CD31 staining (FIG. 6D). Consistent with the targeting of the Blockmir to miR-27-VE-cadherin, there was an increase in the expression of VE-cadherin on the CD31 positive vessels within the ischaemic muscle (data not shown). There was no effect of CD5-2 on capillarnsity in the non-ischaemic muscle (data not shown). Since ischaemic recovery is influenced by both the limitation of oedema and extent of angiogenesis, these results indicate that the Blockmir is influencing both of these aspects. In summary, Blockmir CD5-2 enhanced recovery after ischaemia, even when delivered as a single bolus intravenous injection at the time of the ischaemic insult. Associated with recovery was an inhibition of oedema and an enhancement of the angiogenic response.

Although the Blockmirs described above were designed to target the miR-27a binding site in VE-cadherin, this site is highly homologous in other predicted targets. Therefore the inventors investigated the specificity of the VE-cadherin-directed Blockmir against two other miR-27a verified targets, SEMA6A, and PPARγ (Lin et al., 2009; Zhou et al., 2011). Although anti-mR-27a LNA induced an increase in VE-cadherin and SEMA6A protein expression, consistent with these being target mRNAs, only CD5-2 induced a significant increase in VE-cadherin (FIGS. 7A and 7B). Similarly, the LNA also significantly regulated PPARγ protein expression whereas CD5-2 did not (data no shown). The inventors also used a luciferase reporter assay to investigate the regulation of VE-cadherin using a plasmid containing the entire (1548 bp region) 3'UTR of VE-cadherin. In HeLa cells miR-27a overexpression caused the expected inhibition of VE-cadherin luciferase activity. Blockmir CD5-2 reversed the miR-27a mediated inhibition whereas a Blockmir designed against the miR-27a binding site in PPARγ did not (FIG. 7C). The LNA reversed the inhibition caused by miR-27a overexpression. Mutation of the miR-27 site in VE-cadherin abolished the inhibition by CD5-2. These experiments, using both protein expression and transcriptional reporter assays, demonstrate a degree of selectivity in the design of the Blockmirs, with Blockmir CD5-2 showing activity against VE-cadherin and not for SEMA6A and PPARγ. Further it suggests that although the Blockmir binds to the miR-27a binding site in the 3'UTR of VE-cadherin, it does not activate the miRNA degradative machinery, presumably through lack of recruitment of the necessary accessory protein(s).

Example 6

Blockmirs to VE-Cadherin Inhibit Tumour Growth

In view of the above-described effects of VE-cadherin Blockmirs, the inventors investigated the effect of administration of these Blockmirs on tumour growth in vivo. Syngeneic B16F10 cells ($4 \times 10^5$) in 200 µl PBS were injected subcutaneously into the dorsal right flank region, of C57BL/6 female mice (8 weeks of age). The Blockmir CD5-2 or scrambled control was injected intravenously into mice (three mice per group) when tumours were visible (day 6 after injection of B16F10 cells). Tumour volumes were measured every day with a caliper using the formula: $V = JI \times [d^2 \times D]/6$, where d was the minor tumour axis and D was the major tumour axis. As shown in FIG. 8, in mice administered Blockmir CD5-2 tumour volume increased at a substantially slower rate than in those mice administered the scrambled control Blockmir.

REFERENCES

Achan, V., H. K. Ho, C. Heeschen, M. Stuehlinger, J. J. Jang, M. Kimoto, P. Valiance, and J. P. Cooke. 2005. ADMA regulates angiogenesis: genetic and metabolic evidence. *Vasc Med* 10:7-14.

Gamble, J. R., J. Drew, L. Trezise, A. Underwood, M. Parsons, L. Kasminkas, J. Rudge, G. Yancopoulos, and M. A. Vadas. 2000. Angiopoietin-1 is an antipermeability and anti-inflammatory agent in vitro and targets cell junctions. *Circ Res* 87:603-607.

Gamble, J. R., L. J. Matthias, G. Meyer, P. Kaur, G. Russ, R. Faull, M. C. Berndt, and M. A. Vadas. 1993. Regulation of in vitro capillary tube formation by anti-integrin antibodies. *J Cell Biol* 121:931-943.

Lagos-Quintana, M., R. Rauhut, A. Yalcin, J. Meyer, W. Lendeckel, and T. Tuschl. 2002. Identification of tissue-specific microRNAs from mouse. *Curr Biol* 12:735-739.

Li, X., M. Stankovic, C. S. Bonder, C. N. Hahn, M. Parsons, S. M. Pitson, P. Xia, R. L. Proia, M. A. Vadas, and J. R. Gamble. 2008. Basal and angiopoietin-1-mediated endothelial permeability is regulated by sphingosine kinase-1. *Blood* 111:3489-3497.

Li, X., M. Stankovic, B. P. Lee, M. Aurrand-Lions, C. N. Hahn, Y. Lu, B. A. Imhof, M. A. Vadas, and J. R. Gamble. 2009. JAM-C induces endothelial cell permeability through its association and regulation of {beta}3 integrins. *Arterioscler Thromb Vasc Biol* 29:1200-1206.

Litwin, M., K. Clark, L. Noack, J. Furze, M. Berndt, S. Albelda, M. Vadas, and J. Gamble. 1997. Novel cytokine-independent induction of endothelial adhesion molecules regulated by platelet/endothelial cell adhesion molecule (CD31). *J Cell Biol* 139:219-228.

Medina, J., A. G. Arroyo; F. Sanchez-Madrid, and R. Moreno-Otero. 2004. Angiogenesis in chronic inflammatory liver disease. *Hepatology* 39:1185-1195.

Thomson, J. M., J. Parker, C. M. Perou, and S. M. Hammond. 2004. A custom microarray platform for analysis of microRNA gene expression. *Nat Methods* 1:47-53.

Zhang, G., R. G. Fahmy, N. diGirolamo, and L. M. Khachigian. 2006. JUN siRNA regulates matrix metalloproteinase-2 expression, microvascular endothelial growth and retinal neovascularisation. *J Cell Sci* 119:3219-3226.

Zhou, Q., R. Gallagher, R. Ufret-Vincenty, X. Li, E. N. Olson, and S. Wang. 2011. Regulation of angiogenesis and choroidal neovascularization by members of micro-RNA-23~27~24 clusters. *Proceedings of the National Academy of Sciences of the United States of America* 108:8287-8292.

The invention claimed is:

1. An oligonucleotide comprising a contiguous sequence complementary to at least 12 contiguous bases of SEQ ID NO: 2, wherein the oligonucleotide comprises one or more modified nucleobases, wherein the oligonucleotide is less than 50 nucleotides in length, wherein base-pairing between the oligonucleotide and SEQ ID NO:2 includes positions 22 to 27 of SEQ ID NO:2, and wherein the oligonucleotide can inhibit binding of miR-27a to a RNA molecule comprising SEQ ID NO:2.

2. The oligonucleotide of claim 1, wherein the miR-27a miRNA is hsa-miR-27a comprising the nucleotide sequence set forth in SEQ ID NO:11.

3. The oligonucleotide of claim 1, comprising a contiguous sequence complementary to a sequence of at least or about 13 bases, at least or about 14 bases, at least or about 15 bases, at least or about 16 bases, at least or about 17 bases, at least or about 18 bases, at least or about 19 bases, at least or about 20 bases, at least or about 22 bases, at least or about 25 bases, at least or about 30 bases, or at least or about 35 bases of SEQ ID NO: 2.

4. The oligonucleotide of claim 1, wherein base pairing between the oligonucleotide and SEQ ID NO: 2 includes positions 8-28, 8-27, 9-27, 10-27, 11-27, 12-27, 13-27, 14-27, 15-27, 16-27, 17-27, 18-27, 19-27, 20-27, 21-27, 9-28, 10-28, 11-28, 12-28, 13-28, 14-28, 15-28, 16-28, 17-28, 18-28, 19-28, 20-28 or 21-28 of SEQ ID NO: 2.

5. The oligonucleotide of claim 1, wherein the oligonucleotide comprises the sequence set forth in SEQ ID NO: 3 or SEQ ID NO: 4.

6. The oligonucleotide of claim 1, wherein the one or more modified nucleobases are an LNA nucleobase, a UNA nucleobase or a 2' O-methyl nucleobase.

7. The oligonucleotide of claim 1 comprising a sequence set forth in SEQ ID NO: 5, SEQ ID NO: 6 or SEQ ID NO: 7.

8. A method for modulating the activity of VE-cadherin in a cell, the method comprising contacting the cell with an effective amount of an oligonucleotide of claim 1 to thereby modulate the activity of the VE-cadherin.

9. The method according to claim 8, wherein modulating the activity of VE-cadherin inhibits or reduces vascular permeability, treats or prevents a vascular permeability-associated disease or condition, inhibits tumour growth, treats ischaemic injury, enhances recovery from ischaemic injury, treats surgical wounds and/or promotes post-operative recovery, or promotes or induces angiogenesis.

10. A method for inhibiting or reducing vascular permeability, for treating or preventing a vascular permeability-associated disease or condition, or for inhibiting tumor growth in a subject, the method comprising administering to the subject an effective amount of an oligonucleotide of claim 1.

11. The method of claim 10, wherein the vascular permeability-associated disease or condition is selected from oedema, cardiovascular disease, myocardial infarction, peripheral vascular disease, ischaemia, stroke, cancer, atherosclerosis, psoriasis, diabetes, autoimmune diseases such as rheumatoid arthritis, thrombocytopenia, altitude sickness, barotrauma, iatrogenic disorders, bacterial infections, viral infections, and ocular conditions associated with vascular leak such as non-proliferative and proliferative retinopathies, macular oedema, glaucoma and macular degeneration.

12. The method of claim 11, wherein the oedema is selected from cardiac oedema, pulmonary oedema, renal oedema, macular oedema, cerebral oedema, malnutritional oedema, lymphoedema, or oedema resulting from a surgical procedure.

13. A method for promoting or inducing angiogenesis in cells or tissue of a subject, the method comprising administering to the subject, or to cells or tissue derived therefrom, an effective amount of an oligonucleotide of claim 1.

14. The method of claim 13, wherein the promotion or inducement of angiogenesis is for wound healing, tissue repair, tissue regeneration or tissue engineering.

15. The method of claim 14, wherein the wound is a surgical wound and the angiogenesis is post-operative angiogenesis.

16. The method of claim 15, wherein the surgical wound results from or is associated with dental surgery, cardiac surgery, organ transplantation surgery, knee and hip replacement surgery and limb amputation.

* * * * *

UNITED STATES PATENT AND TRADEMARK OFFICE
CERTIFICATE OF CORRECTION

PATENT NO. : 9,879,255 B2
APPLICATION NO. : 14/433150
DATED : January 30, 2018
INVENTOR(S) : Gamble et al.

It is certified that error appears in the above-identified patent and that said Letters Patent is hereby corrected as shown below:

On the Title Page

In item (73), in "Assignee", in Column 1, Lines 1-2, delete "Assignee: University of Newcastle Upon Tyne, Newcastle Upon Tyne (GB)" and insert --Assignees: The University of Sydney, Sydney (AU); Centenary Institute of Cancer Medicine and Cell Biology, Camperdown (AU); Mirrx Therapeutics A/S, Vejle (DK)-- therefor In item (57), in "Abstract", in Column 2, Line 8, delete "tumor" and insert --tumour-- therefor In the Specification In Column 5, Line 42, delete "as," and insert --as-- therefor In Column 10, Line 55, delete "of," and insert --of-- therefor In Column 11, Line 46, delete "base's," and insert --bases,-- therefor In Column 12, Line 50, delete "5'end" and insert --5'-end-- therefor In Column 12, Line 50, delete "3'end" and insert --3'-end-- therefor In Column 12, Line 59, delete "5'end" and insert --5'-end-- therefor In Column 13, Line 63, delete "3' end." and insert --3'-end.-- therefor In Column 14, Line 33, delete "5'end" and insert --5'-end-- therefor In Column 14, Line 33, delete "3'end" and insert --3'-end-- therefor Signed and Sealed this
Twenty-fourth Day of September, 2019

Andrei Iancu
*Director of the United States Patent and Trademark Office*

CERTIFICATE OF CORRECTION (continued)
U.S. Pat. No. 9,879,255 B2

In Column 14, Line 40, delete "3'end" and insert --3'-end-- therefor

In Column 14, Line 41, delete "5'end" and insert --5'-end-- therefor

In Column 14, Line 57, delete "May" and insert --may-- therefor

In Column 15, Line 34, delete "3' ends" and insert --3'-ends-- therefor

In Column 19, Line 1, delete "days," and insert --days-- therefor

In Column 20, Line 61, delete "hybridzations" and insert --hybridizations-- therefor In Column 21, Line 14, delete "spots," and insert --spots-- therefor In Column 21, Line 16, delete "'Normalize WithinArrays')." and insert --'NormalizeWithinArrays').-- therefor In Column 22, Line 13, delete "Na4P$_2$O$_7$" and insert --Na$_4$P$_2$O$_7$-- therefor In Column 22, Line 40, delete "$\alpha_2\beta_3$-integrin" and insert --$\alpha_2\beta_1$-integrin-- therefor In Column 22, Line 62, delete "Svenules" and insert --venules-- therefor In Column 23, Line 2, delete "UPlanFi" and insert --UPlanFI-- therefor In Column 23, Line 15, delete "10 ug" and insert --10 μg-- therefor In Column 23, Line 60, delete "Abeam)" and insert --Abcam)-- therefor In Column 25, Line 48, delete "Observed." and insert --observed.-- therefor In Column 28, Line 3, delete "region," and insert --region-- therefor In Column 28, Line 19, delete "Valiance," and insert --Vallance,-- therefor In Column 28, Line 51, delete "Arroyo;" and insert --Arroyo,-- therefor